(12) United States Patent
Aydemir et al.

(10) Patent No.: US 10,167,501 B2
(45) Date of Patent: Jan. 1, 2019

(54) METHODS AND APPARATUS FOR QUANTIFICATION OF NUCLEIC ACID AMPLIFICATION BY MONITORING IMPEDANCES

(71) Applicants: Nihan Aydemir, Auckland (NZ); Jadranka Travas-Sejdic, Auckland (NZ); Clive William Evans, Auckland (NZ); David Edward Williams, Auckland (NZ)

(72) Inventors: Nihan Aydemir, Auckland (NZ); Jadranka Travas-Sejdic, Auckland (NZ); Clive William Evans, Auckland (NZ); David Edward Williams, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 419 days.

(21) Appl. No.: 14/738,179

(22) Filed: Jun. 12, 2015

(65) Prior Publication Data

US 2016/0046977 A1 Feb. 18, 2016

Related U.S. Application Data

(60) Provisional application No. 62/011,491, filed on Jun. 12, 2014, provisional application No. 62/146,466, filed on Apr. 13, 2015.

(51) Int. Cl.
*C12Q 1/68* (2018.01)
*G01N 27/02* (2006.01)
*C12Q 1/686* (2018.01)

(52) U.S. Cl.
CPC ............. *C12Q 1/686* (2013.01); *G01N 27/02* (2013.01); *G01N 27/026* (2013.01)

(58) Field of Classification Search
None
See application file for complete search history.

(56) References Cited

U.S. PATENT DOCUMENTS

| | | | |
|---|---|---|---|
| 6,274,351 B1 * | 8/2001 | Peponnet | C12Q 1/6837 435/402 |
| 2005/0181405 A1 * | 8/2005 | Lee | B01L 3/508 435/7.2 |
| 2011/0024309 A1 * | 2/2011 | Lee | G01N 27/3276 205/792 |

OTHER PUBLICATIONS

Kannan et al. Analytical Chemistry 2011; 83: 3415-3421. (Year: 2011).*
Yeung et al. Journal of the American Chemical Society 2006; 128: 13374-13375. (Year: 2006).*
Aydemir, et al., Conducting Polymers for Label Free, Elecgtrochemical, Real-time detection of PCT; School of Chemical Science; 5th Annual Research Showcase on Jun. 12, 2013, Programme & Book of Abstracts.
Aydemir et al., A Label-Free, Sensitive, Real-Time, Semiquantitative Electrochemical Measurement Method for DNA Polymerase Amplification (ePCR); Analytical Chemistry, 2015, 87 (10) pp. 5189-5197.
Aydemir et al., Conducting Polymers for Label Free, Electrochemical, Real-time detection of PCR; School of Chemical Science; 5th Annual research Showcase on Jun. 12, 2013; Programme & Book of Abstracts.
Schrader et al., "PCR inhibitors—occurrence, properties and removal", Journal of Applied Microbiology, 2012, vol. 113, 1014-1026.
Hillman et al., "Role of Film History and Observational Timescale on Redox Switching Kinetics of Electroactive Films Part 1.—A New Model for Permselectiv Films with Polymer Relaxation Processes", J. Chem. Soc. Faraday Trans., 1993, 89(2), 339-348.
Abu Al-Soud et al., "Capacity of Nine Thermostable DNA Polymerases to Mediate DNA Amplification in the Presence of PCR-Inhibiting Samples", Applied and Environmental Microbiology, 1998, 64(10), 3748-3753.
Khalkhali et al., "Effect of Solution Temperature on Electroactivity of Polypyrrole Using Cyclic Voltammetry Technique", Iranian Polymer Journal, 2004, 13(6), 463-470.
Lazaro et al., "Effect of Metal Ions on the Efficiency of DNA Amplification, Implications for Nucleic Acid Replication During Early Stages of Life", Proceedings of the Third European Workshop on Exo-Astrobiology. Mars: The search for Life, Madrid, Spain, 2003, 137-140.
Csahok et al., "In situ dc conductivity study of the redox transformations and relaxation of polyaniline films", Journal of Electroanalytical Chemistry, 2000, vol. 482, 168-177.
Inzelt et al., "Electron and proton conducting polymers: recent developments and prospects", Electrochimica Acta, 2000, vol. 45, 2403-2421.
Odin et al., "Slow Relaxation in Conducting Polymers", Physical Review Letters, 1991, 67(9), 1114-1117.
Inzelt et al., "Conducting Polymers, Monographs in Electrochemistry", Chapter 6 Redox Transformations and Transport Processes, 2012, pp. 191-241, DOI 10.1007/978-3-642-27621-7_6, Springer-Verlag Berlin Heidelberg.

* cited by examiner

*Primary Examiner* — Angela M. Bertagna
(74) *Attorney, Agent, or Firm* — McDonnell Boehnen Hulbert & Berghoff LLP

(57) ABSTRACT

The present invention relates to methods and apparatuses for amplifying, detecting, and optionally quantifying, nucleic acids. In one aspect the method comprises (a) providing a reaction volume comprising (i) a first electrode comprising an electrochemically-active conducting polymer, a first single-stranded nucleic acid molecule capable of hybridizing to a target nucleic acid, wherein the first nucleic acid molecule is covalently attached to the electrochemically-active conducting polymer, and (ii) a second electrode, (b) providing a reaction mixture to the reaction volume, the reaction mixture comprising a target nucleic acid, a nucleic acid polymerase, a redox couple, and nucleic acid amplification reagents, (c) amplifying the nucleic acid, and (d) measuring the impedance of the first electrode at least once during the nucleic acid amplification reaction.

9 Claims, 8 Drawing Sheets
Specification includes a Sequence Listing.

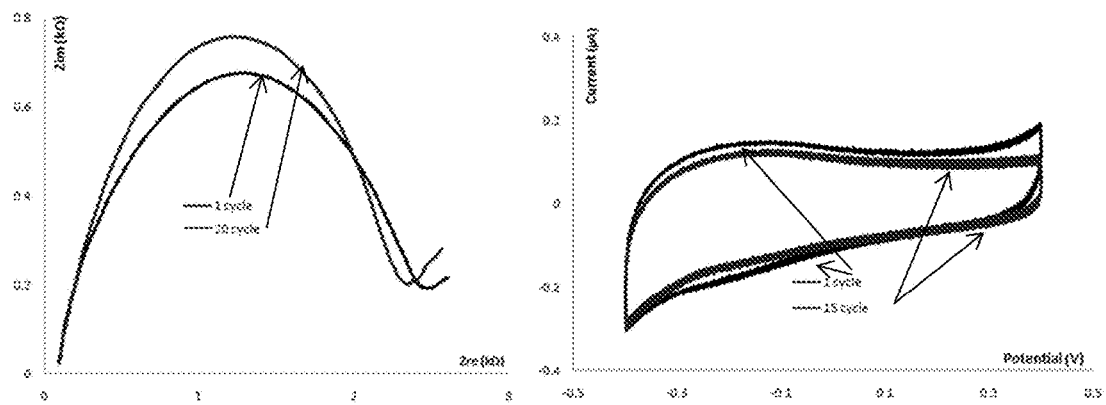
Figure 4A                    Figure 4B
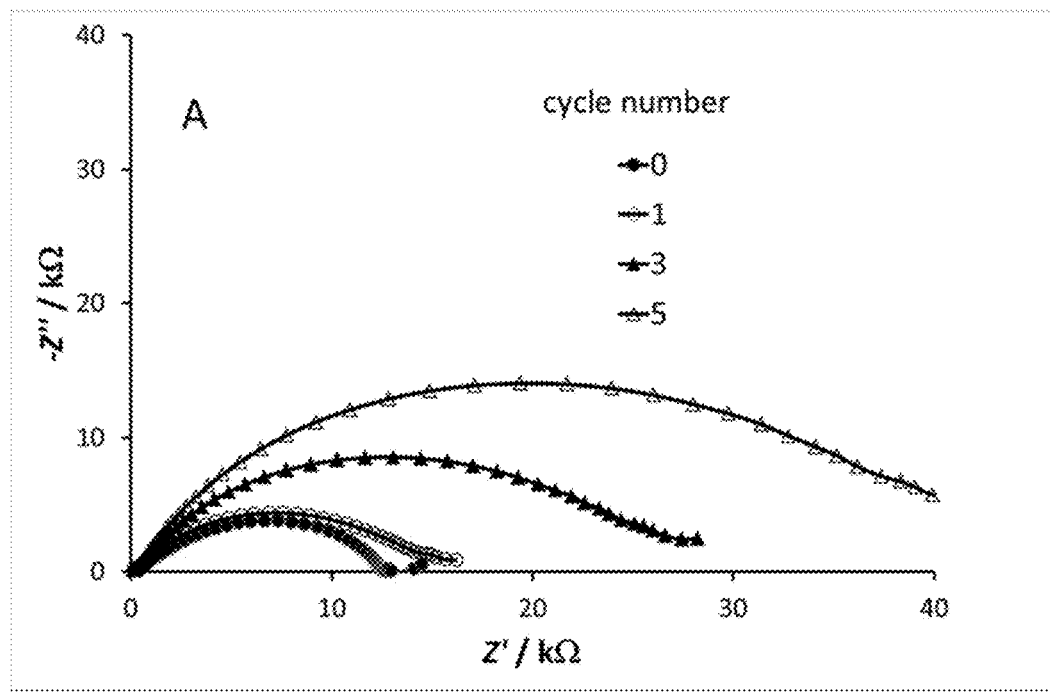
Figure 5A

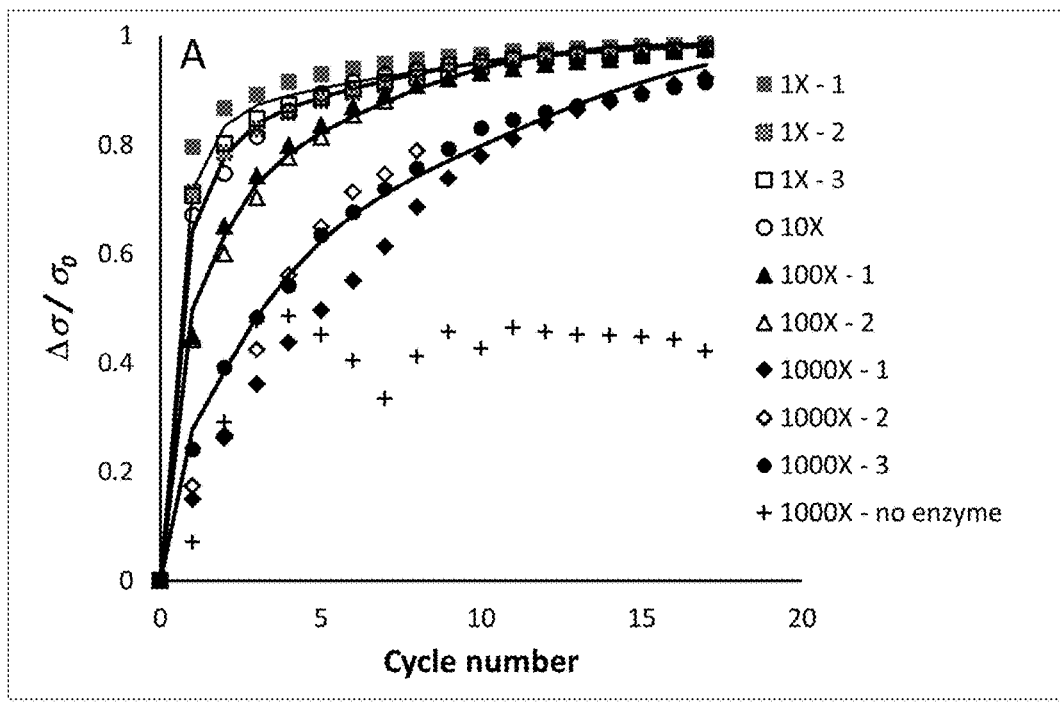
Figrue 6A
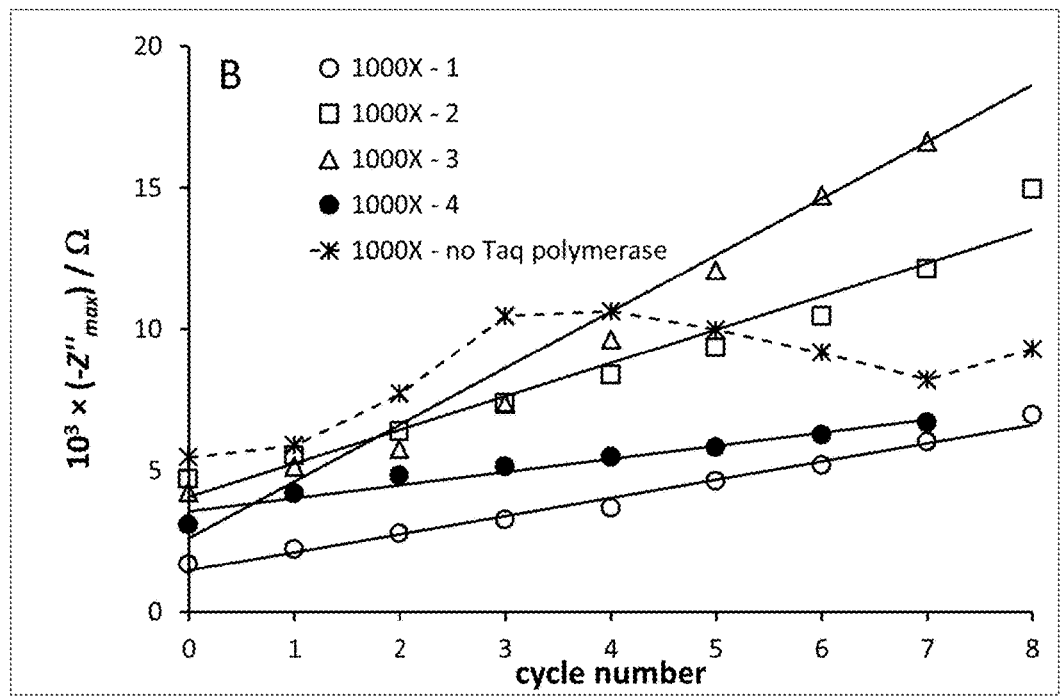
Figure 6B

Denature : state 2 -> state 0; state 3 -> state 1
Anneal   : state 0 -> state 2; state 1 -> state 3
Extend   : state 2 -> state 3

METHODS AND APPARATUS FOR QUANTIFICATION OF NUCLEIC ACID AMPLIFICATION BY MONITORING IMPEDANCES

FIELD OF THE INVENTION

The present invention relates to methods and apparatuses for amplifying, detecting, and optionally quantifying, nucleic acids.

BACKGROUND TO THE INVENTION

The detection, identification and quantification of nucleic acids is central to a number of technologies having application in diverse industries including the medical, agricultural, pharmaceutical, biotechnological, and security fields.

Real time polymerase chain reaction (RT-PCR) is a powerful technology for such detection, identification, and quantification of nucleic acids. Traditional RT-PCR methods measure total DNA using fluorescent intercalation dyes or labelled primers. Electrochemical measurement in principle offers many advantages, in instrumentation, measurement system design and cost of implementation. There have been a number of reports of coupling of electrochemical measurement with PCR amplification. These methods, again, have either used intercalation reagents for non-specific measurement or electrochemical labels on the primers or nucleotides. The sensitivity (signal/noise or signal/background) of the measurement technique determines the number of cycles of amplification required to obtain a reliable signal, which in turn determines the time to result and also the influence of replication errors.

There remains a need for methods of detecting amplified nucleic acid at high sensitivity, and particularly methods that are robust and reliable and/or amenable to implementation in high throughput or microfluidic systems.

The present invention is directed to providing methods and apparatuses for amplifying, detecting and/or quantifying nucleic acids, or to at least provide the public with a useful choice.

SUMMARY OF THE INVENTION

In a first aspect the invention relates to a method for amplifying a target nucleic acid, the method comprising the steps of
a) providing a reaction volume comprising
  (i) a first electrode comprising an electrochemically-active conducting polymer,
  (ii) a first single-stranded nucleic acid molecule capable of hydridizing to a first portion of a target nucleic acid sequence, wherein the first nucleic acid molecule is covalently attached to the electrochemically-active conducting polymer, and
  (iii) a second electrode;
b) providing a reaction mixture to the reaction volume, the reaction mixture comprising
  (i) the target nucleic acid,
  (ii) optionally a second single-stranded nucleic acid molecule comprising nucleic acid sequence complementary to a second portion of the target nucleic acid sequence,
  (iii) a nucleic acid polymerase,
  (iv) a redox couple, and
  (v) a supply of reagents for a nucleic acid amplification reaction;
c) performing a nucleic acid amplification reaction, for example a polymerase chain reaction, and
d) measuring the impedance of the first electrode at least once during the nucleic acid amplification reaction.

In one embodiment, the method comprises the additional step of
e) determining the amount of polynucleotide present in the reaction volume on the basis of the one or more impedance measurements.

In a second aspect the invention relates to a method for determining the presence or amount of nucleic acid in a sample, the method comprising the steps of
a) providing a reaction volume comprising
  (i) a first electrode comprising an electrochemically-active conducting polymer,
  (ii) a first single-stranded nucleic acid molecule capable of hydridizing to a first portion of a target nucleic acid sequence, wherein the first nucleic acid molecule is covalently attached to the electrochemically-active conducting polymer, and
  (iii) a second electrode;
b) providing a reaction mixture to the reaction volume, the reaction mixture comprising
  (i) the target nucleic acid,
  (ii) optionally a second single-stranded nucleic acid molecule comprising nucleic acid sequence complementary to a second portion of the target nucleic acid sequence,
  (iii) a nucleic acid polymerase,
  (iv) a redox couple, and
  (v) a supply of reagents for a nucleic acid amplification reaction;
c) performing a nucleic acid amplification reaction, for example a polymerase chain reaction,
d) measuring the impedance of the first electrode at least once during the nucleic acid amplification reaction, and
e) determining the amount of polynucleotide present in the reaction volume on the basis of the one or more impedance measurements.

In one embodiment, the method comprises the additional step of measuring the impedance of the first electrode before the first elongation step of the nucleic acid amplification reaction, for example before the first elongation step of a polymerase chain reaction.

In one embodiment, the method comprises the steps of
a) providing a reaction volume comprising
  (i) a first electrode comprising an electrochemically-active conducting polymer,
  (ii) a first single-stranded nucleic acid molecule capable of hydridizing to a first portion of a target nucleic acid sequence, wherein the first nucleic acid molecule is covalently attached to the electrochemically-active conducting polymer, and
  (iii) a second electrode;
b) providing a reaction mixture to the reaction volume, the reaction mixture comprising
  (i) the target nucleic acid,
  (ii) a second single-stranded nucleic acid molecule comprising nucleic acid sequence complementary to a second portion of the target nucleic acid sequence,
  (iii) a nucleic acid polymerase,
  (iv) a redox couple, and
  (v) a supply of reagents for a nucleic acid amplification reaction;
c) performing a nucleic acid amplification reaction, for example a polymerase chain reaction, d) measuring the impedance of the first electrode at least once during the nucleic acid amplification reaction, and
e) determining the amount of polynucleotide present in the reaction volume on the basis of the one or more impedance measurements.

In one embodiment, the method comprises the steps of
a) providing a reaction volume comprising
   (i) a first electrode comprising an electrochemically-active conducting polymer,
   (ii) a first single-stranded nucleic acid molecule capable of hydridizing to a first portion of a target nucleic acid sequence, wherein the first nucleic acid molecule is covalently attached to the electrochemically-active conducting polymer, and
   (iii) a second electrode;
b) providing a reaction mixture to the reaction volume, the reaction mixture comprising
   (i) the target nucleic acid,
   (ii) a second single-stranded nucleic acid molecule comprising nucleic acid sequence complementary to a second portion of the target nucleic acid sequence,
   (iii) the first single-stranded nucleic acid molecule, or a single-stranded nucleic acid molecule capable of hydridizing to the first portion of the target nucleic acid sequence.
   (iv) a nucleic acid polymerase,
   (v) a redox couple, and
   (vi) a supply of reagents for a nucleic acid amplification reaction;
c) performing a nucleic acid amplification reaction, for example a polymerase chain reaction,
d) measuring the impedance of the first electrode at least once during the nucleic acid amplification reaction, and
e) determining the amount of polynucleotide present in the reaction volume on the basis of the one or more impedance measurements.

In a third aspect the invention relates to an apparatus for amplifying nucleic acid in accordance with a method of the present invention.

In one embodiment, the apparatus is an apparatus for real-time nucleic acid amplification, for example a polymerase chain reaction, the apparatus comprising
a reaction volume comprising
   (i) a first electrode comprising an electrochemically-active conducting polymer, wherein the electrochemically-active conducting polymer is capable of being covalently bound by a single stranded nucleic acid molecule,
   (ii) optionally a first single-stranded nucleic acid molecule capable of hydridizing to a first portion of a target nucleic acid sequence, wherein the first nucleic acid molecule is covalently attached to the electrochemically-active conducting polymer, and
   (iii) a second electrode;
   wherein the reaction volume is suitable for containing a sample comprising nucleic acid, and wherein the reaction volume includes a heater or is adapted to engage with a thermocycler suitable for PCR.

In one embodiment, the apparatus is an apparatus for real-time nucleic acid amplification reaction, for example a polymerase chain reaction, the apparatus comprising
a reaction volume comprising
   (i) a first electrode comprising an electrochemically-active conducting polymer, wherein the electrochemically-active conducting polymer is capable of being covalently bound by a single stranded nucleic acid molecule,
   (ii) optionally a first single-stranded nucleic acid molecule capable of hydridizing to a first portion of a target nucleic acid sequence, wherein the first nucleic acid molecule is covalently attached to the electrochemically-active conducting polymer, and
   (iii) a second electrode;
   wherein the reaction volume is suitable for containing a sample comprising nucleic acid, and wherein the reaction volume is adapted to engage with a thermocycler suitable for PCR, and a device for measuring impedance of at least the first electrode.

In one embodiment, the apparatus is an apparatus for real-time nucleic acid amplification reaction, for example a polymerase chain reaction, the apparatus comprising
a reaction volume comprising
   (i) a first electrode comprising an electrochemically-active conducting polymer, wherein the electrochemically-active conducting polymer is capable of being covalently bound by a single stranded nucleic acid molecule,
   (ii) optionally a first single-stranded nucleic acid molecule capable of hydridizing to a first portion of a target nucleic acid sequence, wherein the first nucleic acid molecule is covalently attached to the electrochemically-active conducting polymer, and
   (iii) a second electrode;
   wherein the reaction volume is suitable for containing a sample comprising nucleic acid, and wherein the reaction volume is adapted to engage with a thermocycler suitable for PCR, and a thermocycler suitable for PCR.

In one embodiment, the apparatus is an apparatus for real-time nucleic acid amplification reaction, for example a polymerase chain reaction, the apparatus comprising
a reaction volume comprising
   (i) a first electrode comprising an electrochemically-active conducting polymer, wherein the electrochemically-active conducting polymer is capable of being covalently bound by a single stranded nucleic acid molecule,
   (ii) optionally a first single-stranded nucleic acid molecule capable of hydridizing to a first portion of a target nucleic acid sequence, wherein the first nucleic acid molecule is covalently attached to the electrochemically-active conducting polymer, and
   (iii) a second electrode;
   wherein the reaction volume is suitable for containing a sample comprising nucleic acid, and wherein the reaction volume is adapted to engage with a thermocycler suitable for PCR,
a thermocycler suitable for PCR, and a device for measuring the impedance of at least the first electrode.

In various embodiments, the electrode comprises an electrochemically-active conducting polymer covalently bound by a single stranded nucleic acid molecule capable of hydridizing to a first portion of a target nucleic acid sequence.

In a further aspect the invention relates to a system for amplifying a target nucleic acid in a sample, the system comprising
a) a reaction volume comprising
   (i) a first electrode comprising an electrochemically-active conducting polymer, wherein the electrochemically-active conducting polymer is capable of being covalently bound by a single stranded nucleic acid molecule,
   (ii) optionally a first single-stranded nucleic acid molecule capable of hydridizing to a first portion of a target nucleic acid sequence, wherein the first nucleic acid molecule is covalently attached to the electrochemically-active conducting polymer, and
(iii) a second electrode;
b) optionally a reaction mixture comprising one or more of
(i) a second single-stranded nucleic acid molecule comprising nucleic acid sequence complementary to a second portion of the target nucleic acid sequence,
(ii) a nucleic acid polymerase,
(iii) a redox couple, and
(iv) a supply of reagents for a nucleic acid amplification reaction;
c) a device for measuring the impedance of at least the first electrode; and
d) a thermocycler.

In one embodiment the system comprises a reaction mixture comprising each of (i) to (iv) above.

In one embodiment, the system comprises multiple reaction volumes. In one embodiment, the system comprises multiple reaction volumes wherein two or more of the reaction volumes comprises the same first nucleic acid molecule. In one embodiment, the system comprises multiple reaction volumes wherein one or more of the reaction volumes comprise a different first nucleic acid molecule. For example, the system comprises multiple reaction volumes wherein each of the reaction volumes comprises a different first nucleic acid molecule.

In a further aspect, the invention relates to a method of preparing an electrode comprising an electrochemically-active conducting polymer, the method comprising
providing an electrode and one or more pyrroles and/or one or more pyrrolylacrylic acids and/or one or more pyrrolylbutyric acids in a substantially aqueous solvent,
providing an electric current through the electrode to polymerise the one or more pyrroles and/or the one or more pyrrolylacrylic acids and/or one or more pyrrolylbutyric acids,
optionally monitoring or measuring electrical impedance of the electrode or charge passed through the electrode,
thereby coating the electrode with the electrochemically-active conducting polymer.

In one embodiment, the substantially aqueous solvent comprises organic solvent.

In one embodiment, the substantially aqueous solvent comprises one or more ions present in a PCR buffer. For example, the substantially aqueous solvent comprises one or more chloride ions, one or more potassium ions, or both potassium and chloride ions.

In one embodiment, the method comprises measuring cumulative charge passed through the electrode. In one embodiment, the method comprises measuring cumulative charge passed through the electrode and terminating the polymerisation on the basis of the measurement. For example, the method comprises measuring cumulative charge passed through the electrode and terminating the polymerisation when a total charge of from about $1.0 \times 10^{-5}$ C to about $5 \times 10^{-5}$ C is measured.

Any one or more of the following embodiments may relate to any of the aspects herein.

In one embodiment the reaction volume is an electrochemical cell. In one embodiment the reaction volume is a microfluidic cell. In one embodiment the reaction volume is a vessel selected from a vessel provided with tubes or a multi-well plate, a Petri dish, a slide, a Terasaki plate, or a PCR plate.

In one embodiment, the electrochemically-active conducting polymer is thermostable. For example, transconductance across the polymer in the absence of nucleic acid amplification differs by less than about 5% over a PCR cycle.

In one embodiment the electrochemically-active conducting polymer is or comprises a poly-pyrrole or a derivative thereof. For example, the electrochemically-active conducting polymer is or comprises pyrrolylacrylic acid, for example poly-3-pyrrolylacrylic acid, is or comprises pyrrolylbutyric acid, for example poly-4-(3-pyrrolyl)butyric acid, or is or comprises a co-polymer of poly-pyrrole and 3-pyrrolacrylic acid, or is or comprises a co-polymer of poly-pyrrole and 4-(3-pyrrolylbutyric) acid.

In one embodiment, the electrochemically-active conducting polymer is or comprises a poly-thiophene or a derivative thereof. For example, the electrochemically-active conducting polymer is or comprises 3,4-ethylenedioxythiophene, or is or comprises poly(3,4-ethylenedioxythiophene).

In one embodiment, the electrochemically-active conducting polymer is or comprises a poly-aniline or a derivative thereof.

In one embodiment, the electrochemically-active conducting polymer comprises both pyrrole and thiophene. For example, the electrochemically-active conducting polymer is or comprises 2-(2,5-di(pyrrol-2-yl)thiophen-3-yl) ethyl 2-bromopropanoate).

In one embodiment, the electrochemically-active conducting polymer is present on the electrode as a porous layer.

In one embodiment the redox couple is ferro-ferricyanide. For example, the redox couple is $(Fe(CN)_6^{3-/4-})$.

In one embodiment, the redox couple is not a DNA intercalator.

In various embodiments, the first single-stranded nucleic acid molecule, the second single-stranded nucleic acid molecule, or both the first and the second single stranded nucleic acid molecules is a single-stranded oligonucleotide probe or primer.

In one embodiment, the reaction mixture additionally comprises the first single-stranded nucleic acid molecule, or a single-stranded nucleic acid molecule capable of hybridizing to the first portion of the target nucleic acid sequence.

In one embodiment, the reaction mixture additionally comprises the second single-stranded nucleic acid molecule, or a single-stranded nucleic acid molecule complementary to the second portion of the target nucleic acid sequence.

In one embodiment, the reaction mixture additionally comprises the first single-stranded nucleic acid molecule or a single-stranded nucleic acid molecule capable of hybridizing to the first portion of the target nucleic acid sequence, and the second single-stranded nucleic acid molecule or a single-stranded nucleic acid molecule complementary to the second portion of the target nucleic acid sequence, or any combination thereof.

In various embodiments, the nucleic acid amplification reaction is catalysed by a nucleic acid polymerase. In one embodiment, the nucleic acid amplification reaction is a polymerase chain reaction.

In one embodiment, the nucleic acid polymerase is a DNA polymerase, for example, a thermostable DNA polymerase.

In one embodiment, the nucleic acid polymerase is an RNA polymerase, for example, a thermostable RNA polymerase.

In one embodiment the reaction mixture comprises, or the polymerase chain reaction is carried out in the presence of, a reverse transcriptase such that the polymerase chain reaction is reverse-transcription polymerase chain reaction and wherein the one or more polynucleotide sequences is obtained from mRNA derived from the sample.

In various embodiments, multiple impedance measurements are made. In various embodiments, one or more impedance measurements is carried out at one or more frequencies. In various embodiments, one or more impedance measurements are carried out across a range of frequencies.

In one embodiment, the impedance is measured more than once during the polymerase chain reaction. In one embodiment, the impedance is measured at least once per cycle of the polymerase chain reaction.

In one embodiment, the impedance is measured continuously throughout at least a portion of the polymerase chain reaction, for example, the impedance is measured continuously throughout a cycle of the polymerase chain reaction. In one example, the impedance is measured continuously throughout multiple cycles of the polymerase chain reaction.

In one embodiment, the impedance is measured during one or more of the annealing, elongation, or dissociation steps of the polymerase chain reaction.

In one embodiment, one or more impedance measurements are made during each of the annealing steps of the polymerase chain reaction.

In one embodiment, one or more impedance measurements are made during each of the elongation steps of the polymerase chain reaction.

In one embodiment, one or more impedance measurements are made during each of the dissociation steps of the polymerase chain reaction.

In one embodiment, the device for measuring impedance is an LCR meter. In one embodiment the device for measuring impedance is a potentiostat.

In one embodiment, impedance is measured by determining the transconductance of or at the first electrode.

In one embodiment, impedance is measured by cyclic voltammetry.

In one embodiment, the method is capable of determining the presence of a target nucleic acid in a sample, wherein the target nucleic acid is present at an initial concentration of less than $10^{-15}$ M. In one embodiment, the target nucleic acid is present at an initial concentration of less than about $10^{-18}$ M.

In one embodiment, the method is capable of determining the amount of a target nucleic acid in a sample, wherein the target nucleic acid is present at an initial concentration of less than $10^{-15}$ M. In one embodiment, the target nucleic acid is present at an initial concentration of less than about $10^{-18}$ M.

In one embodiment, the method is capable of determining the presence or amount of a target nucleic acid in a sample, wherein the target nucleic acid is present at an initial concentration of less than $10^{-15}$ M, and wherein the polymerase chain reaction comprises fewer than 20 PCR cycles. In one example, the polymerase chain reaction comprises fewer than 15 PCR cycles. In another example, the polymerase chain reaction comprises fewer than 10 PCR cycles.

In one embodiment, the method is capable of determining the presence or amount of a target nucleic acid in a sample, wherein the target nucleic acid is present at an initial concentration of less than $10^{-18}$ M, and wherein the polymerase chain reaction comprises fewer than 20 PCR cycles. In one example, the polymerase chain reaction comprises fewer than 15 PCR cycles. In another example, the polymerase chain reaction comprises fewer than 10 PCR cycles.

In one embodiment, the method is capable of determining the presence or amount of a target nucleic acid in a sample comprising other nucleic acid, wherein the target nucleic acid is present at an initial mass ratio of target sequence to total nucleic acid of less than about $1.5\times10^{-3}$. In one example, the initial mass ratio of target sequence to total nucleic acid is less than about $2\times10^{-3}$. In one example, the initial mass ratio of target sequence to total nucleic acid is less than about $2.5\times10^{-3}$.

In various embodiments, the method is capable of determining the presence or amount of a target nucleic acid in a sample comprising other nucleic acid, wherein the target nucleic acid is present at an initial mass ratio of target sequence to total nucleic acid of less than about $1\times10^{-4}$. For example, the initial mass ratio of target sequence to total nucleic acid is less than about $1\times10^{-5}$, or the initial mass ratio of target sequence to total nucleic acid is less than about $1\times10^{-6}$.

In one embodiment, the method is capable of determining the presence or amount of a target nucleic acid in a sample, wherein the target nucleic acid is present at an initial concentration of less than 1 pg/mL. For example, the target nucleic acid is present at an initial concentration of less than about 500 fg/mL, less than about 400 fg/mL, less than about 300 fg/mL, less than about 200 fg/mL, less than about 150 fg/mL, or less than about 100 fg/mL. In still further examples, the target nucleic acid is present at an initial concentration of less than about 50 fg/mL, less than about 40 fg/mL, less than about 30 fg/mL, less than about 20 fg/mL, less than about 10 fg/mL, less than about 7.5 fg/mL, less than about 5 fg/mL, less than about 2.5 fg/mL, less than about 2 fg/mL, less than about 1.5 fg/mL, less than about 1.25 fg/mL, or less than about 1 fg/mL.

In one embodiment, the method is capable of determining the presence or amount of a target nucleic acid in a sample comprising other nucleic acid, wherein the target nucleic acid is present at an initial concentration of less than 1 pg/mL. For example, the target nucleic acid is in a sample comprising other nucleic acid and is present at an initial concentration of less than about 500 fg/mL, less than about 400 fg/mL, less than about 300 fg/mL, less than about 200 fg/mL, less than about 150 fg/mL, or less than about 100 fg/mL. In still further examples, the target nucleic acid is in a sample comprising other nucleic acid and is present at an initial concentration of less than about 50 fg/mL, less than about 40 fg/mL, less than about 30 fg/mL, less than about 20 fg/mL, less than about 10 fg/mL, less than about 7.5 fg/mL, less than about 5 fg/mL, less than about 2.5 fg/mL, less than about 2 fg/mL, less than about 1.5 fg/mL, less than about 1.25 fg/mL, or less than about 1 fg/mL.

In one embodiment, the method is capable of determining the presence or amount of a target nucleic acid in a sample, including in a sample comprising other nucleic acid, wherein the target nucleic acid is present at an initial concentration of less than 1 pg/mL, and wherein the polymerase chain reaction comprises fewer than 20 PCR cycles. For example, the target nucleic acid is present at an initial concentration of less than about 500 fg/mL and the polymerase chain reaction comprises fewer than 20 PCR cycles, less than about 400 fg/mL and the polymerase chain reaction comprises fewer than 20 PCR cycles, less than about 300 fg/mL and the polymerase chain reaction comprises fewer than 20 PCR cycles, less than about 200 fg/mL and the polymerase chain reaction comprises fewer than 20 PCR cycles, less than about 150 fg/mL and the polymerase chain reaction comprises fewer than 20 PCR cycles, or less than 100 fg/mL and the polymerase chain reaction comprises fewer than 20 PCR cycles. In various embodiments, the polymerase chain reaction comprises fewer than 15 PCR cycles, for example, the polymerase chain reaction comprises fewer than 10 PCR cycles.

For example, the target nucleic acid is present at an initial concentration of less than about 50 fg/mL and the polymerase chain reaction comprises fewer than 20 PCR cycles, less than about 40 fg/mL and the polymerase chain reaction comprises fewer than 20 PCR cycles, less than about 30 fg/mL and the polymerase chain reaction comprises fewer than 20 PCR cycles, less than about 20 fg/mL and the polymerase chain reaction comprises fewer than 20 PCR cycles, less than about 15 fg/mL and the polymerase chain reaction comprises fewer than 20 PCR cycles, less than 10 fg/mL and the polymerase chain reaction comprises fewer than 20 PCR cycles, less than 7.5 fg/mL and the polymerase chain reaction comprises fewer than 20 PCR cycles, less than 5 fg/mL and the polymerase chain reaction comprises fewer than 20 PCR cycles, less than 2.5 fg/mL and the polymerase chain reaction comprises fewer than 20 PCR cycles, less than 2 fg/mL and the polymerase chain reaction comprises fewer than 20 PCR cycles, less than 1.5 fg/mL and the polymerase chain reaction comprises fewer than 20 PCR cycles, less than 1.25 fg/mL and the polymerase chain reaction comprises fewer than 20 PCR cycles, or less than 1 fg/mL and the polymerase chain reaction comprises fewer than 20 PCR cycles. In various embodiments, the polymerase chain reaction comprises fewer than 15 PCR cycles, for example, the polymerase chain reaction comprises fewer than 10 PCR cycles.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

BRIEF DESCRIPTION OF THE FIGURES

FIG. 2C) an acceptable electrode preparation; and FIG. 2D) a graph showing electrochemical impedance measured at 72° C. in the 2-terminal electrochemical cell at +0.23 V cell potential difference in the above buffer confirming successful attachment of the probe sequence from the resultant increase in impedance. FIG. 2D) Inset: approximate equivalent circuit: solution resistance between working and counter/reference electrode is Rs, constant phase element describing the capacitive behaviour of the ECP-coated electrode is Q, charge transfer resistance for the reaction of the redox couple is RCT and impedance contributed by diffusion of the redox couple to the electrode is W.

FIG. 3A) 7×10$^{-3}$, 20. FIG. 3B) 2.5×10$^{-2}$, 25. FIG. 3C) 0.4, 25. DNA was visualised using RedSafe™, Nucleic Acid Staining solution.

FIGS. 4A-4B show the stability of the ECP-modified electrode under temperature cycling according to the PCR regime, in the absence of target DNA. Measurements were made at 72° C. FIG. 4A) Nyquist diagram of the ECP-modified, primer-attached electrode in the presence of 5 mM redox couple in the 2-terminal electrochemical cell at +0.23 V cell potential difference, FIG. 4B) Cyclic voltammetry of the ECP-modified electrode without attached template in the absence of redox couple.

FIGS. 5A-5C show amplification with surface-attached primer only. Measurements at 72° C. following extension, in the presence of 5 mM redox couple in the 2-terminal electrochemical cell at +0.23 V cell potential difference. Undiluted mixed sample DNA, 1.2 ng/μL (see Table 1). FIG. 5A) evolution of Nyquist diagram with cycle number; FIG. 5B) imaginary impedance component, −Z″, against measurement frequency, f and evolution with cycle number; FIG. 5C) evolution of relative reaction conductance (eq 1) with cycle number, where the line is fitted to a simple 2-state model.

FIGS. 6A-6B show FIG. 6A) relative reaction conductance (eq 2) and FIG. 6B) reaction impedance for the first cycles for the 1000× dilution including the initial measurement of the template-modified electrode and the Taq polymerase-free blank, for the 3-primer system. Measurements at 72° C. following extension, in the presence of 5 mM redox couple and 7×10$^{-3}$ unit/μL Taq polymerase in the 2-terminal electrochemical cell at +0.23 V cell potential difference. The effect of dilution of the original mixed DNA sample is shown: from 1.2 ng/μL (1× dilution) to 1.2 pg/μL (1000× dilution, target DNA present at 1 part in 10$^6$ total DNA). The lines in A) are a fit to a 4-state model (see Discussion). The repeat measurements shown are for independent electrode preparations.

DETAILED DESCRIPTION OF THE INVENTION

Figure 1:
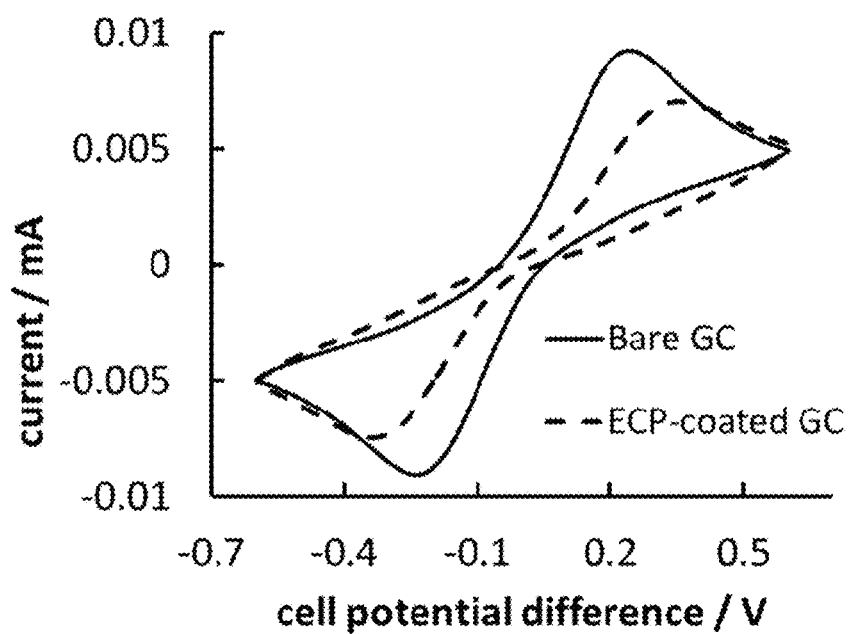
FIG. 1 is a graph showing the results of cyclic voltammetry (scan rate 0.1 V/s) at 72° C. in the 2-terminal electrochemical cell, of 5 mM Fe(CN)$_6^{-3/-4}$ in PCR buffer (20 mM Tris-HCl, pH 8.4, 50 mM KCl) containing 2.5 mM MgCl$_2$, comparing the bare GC electrode with an electrode modified with a thin film of ECP.
Figure 2A:
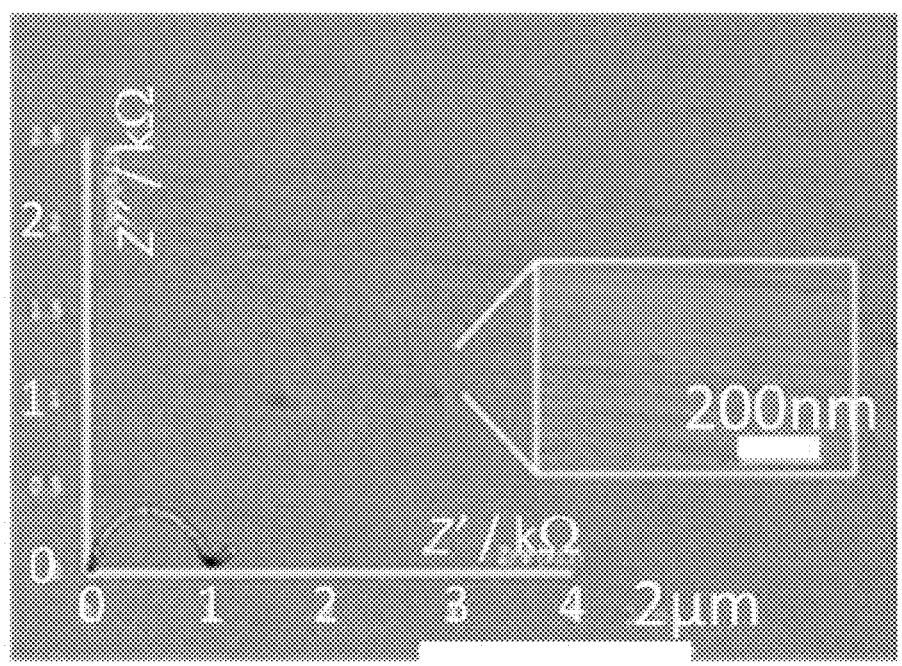
FIGS. 2A-2D show scanning electron micrograph (SEM) images and corresponding Nyquist diagrams, measured at 72° C. in the 2-terminal electrochemical cell in PCR buffer containing 5 mM Fe(CN)$_6^{-3/-4}$ and 2.5 mM MgCl$_2$, where FIG. 2A) bare GC surface, FIG. 2B) a rejected electrode preparation.
Figure 2B:
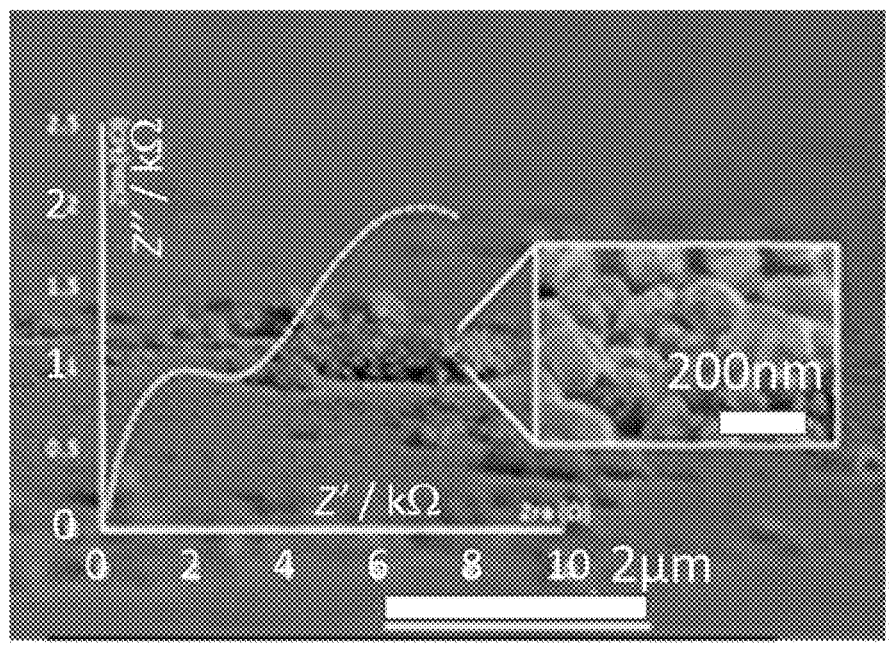
Figure 2C:
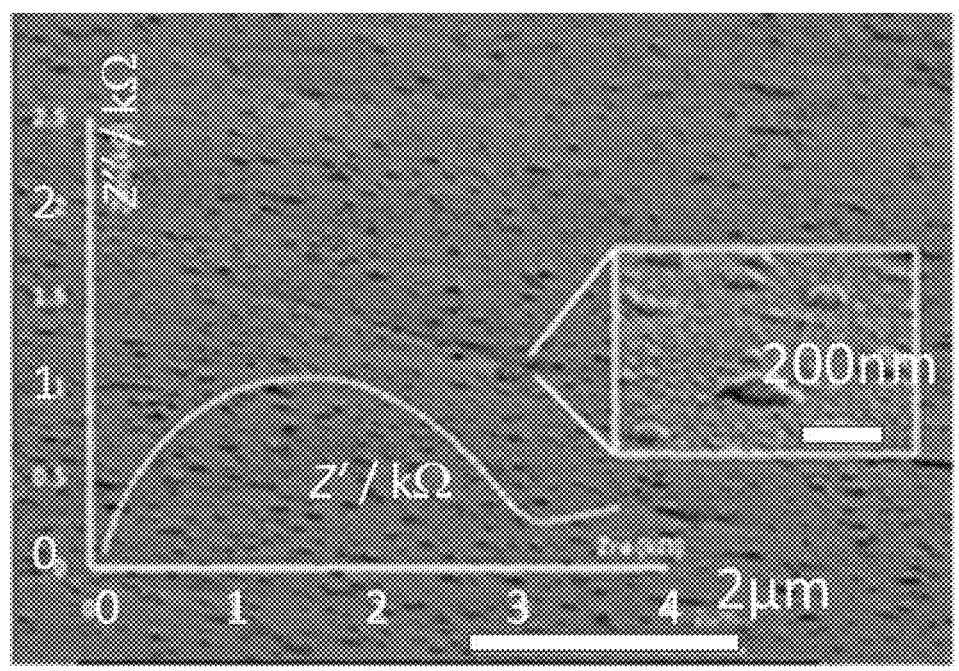
Figure 2D:
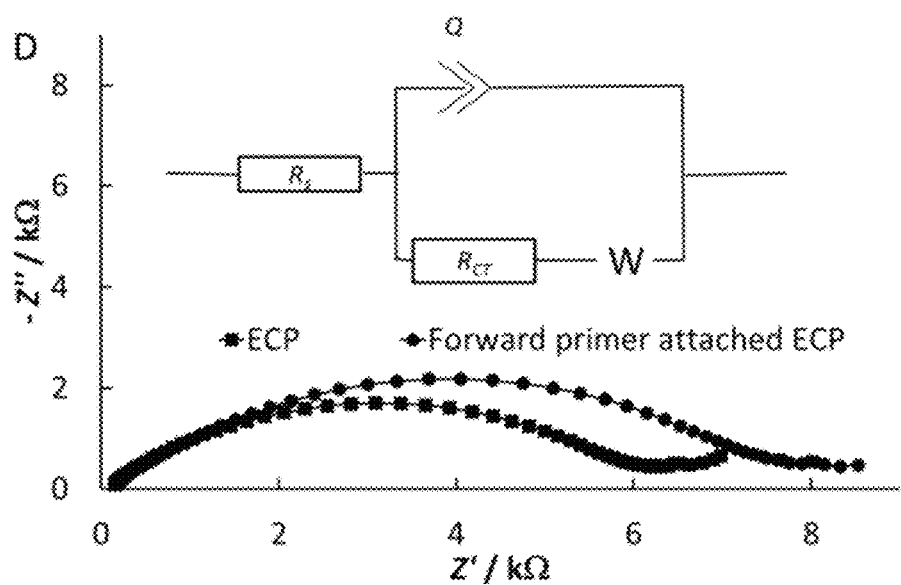

The present invention relates to methods, systems and apparatuses for amplifying, detecting, identifying and/or quantifying nucleic acids. The present invention provides for the highly sensitive amplification and label-free detection of nucleic acids by real-time nucleic acid amplification, for example by polymerase chain reaction (PCR).

Those skilled in the art will understand that the term "real-time nucleic acid amplification reaction" contemplates the monitoring in real time of the amplification of nucleic acid, for example by elongation catalysed by a nucleic acid polymerase, for example in a polymerase chain reaction.

Those skilled in the art will understand that the terms "real-time polymerase chain reaction", "real-time PCR", and "RT-PCR are used interchangeably herein and contemplate the monitoring in real time of the amplification of nucleic acid by the polymerase chain reaction.

A polymerase chain reaction typically comprises the repeated steps of annealing a forward and a reverse probe to target nucleic acid, elongation, and dissociation. In one embodiment, the PCR of the methods of the invention involves
optionally maintaining the reaction volume or PCR reaction mixture for a period and at a temperature sufficient to allow initial dissociation of the target nucleic acid, followed by repeated cycles of
maintaining the reaction volume or the PCR reaction mixture for a period and at a temperature sufficient to allow hybridisation of the target nucleic acid to forward and reverse primers,
maintaining the reaction volume or the PCR reaction mixture for a period at a temperature sufficient to allow elongation of the forward and reverse primers by polymerization,
maintaining the reaction volume or the PCR reaction mixture for a period at a temperature sufficient to allow dissociation of the nucleic acid duplex,
thereby to provide amplified nucleic acid.

Those skilled in the art will appreciate that the reagents for a nucleic acid amplification reaction will typically include buffers, and nucleotides, particularly nucleotide triphosphates such as dATP, dCTP, dGTP or dTTP.

As will be appreciated by those skilled in the art on reading the specification, target nucleic acid specificity can be readily achieved by appropriate selection of the nucleic acid primers covalently bound to the electrode and present in the reaction mixture.

The present invention provides highly sensitive real-time PCR using electrochemical detection and/or measurement in the presence of one or more redox couples, via an electrode comprising electrochemically-active conducting polymer to which is covalently bound one or more nucleic acid primers. The electrode is present in a reaction volume in which the polymerase chain reaction takes place.

In various embodiments, the reaction volume comprises an electrochemical cell, such as a miniature electrochemical cell. In one embodiment, the electrochemical cell comprises a heat source, such as an embedded heater, and two electrodes, for example two printed carbon electrodes. It will be apparent to a person skilled in the art on reading this specification that one of the electrodes is the working (or detection) electrode, comprising the electrochemically-active conducting polymer and surface bound primer, and the other electrode is the reference or counter electrode.

In one embodiment, the reaction volume is in the form of a miniature well, such as that present on a microtitre plate. In one embodiment, the invention provides multiple reaction volumes, for example multiple wells, having a single heater or thermocycler. In one embodiment each reaction volume, for example each well, is individually addressable and may be configured to amplify the same target sequence thereby to achieve redundancy of measurement for improved accuracy, or to amplify a different target sequence thereby to have multiple analyte capability.

In one embodiment, the real-time PCR system comprises multiple reaction volumes provided with a corresponding heating portion and a detector for detecting the impedance of the first electrode. In certain embodiments, each reaction volume is provided with a controller for controlling temperatures of the individual heating regions independently with high accuracy.

In one embodiment, the reaction volumes for PCR reactions are desirably in the form of microcavities. For example, in one embodiment the reaction volume is in the nanoliter volume range, so as to allow for extremely high density arrays of reaction volumes.

In one embodiment the reaction volume is associated with a Peltier element to perform heating, cooling, and/or temperature control.

In one embodiment, the detection electrode is prepared as follows: the electrochemically-active copolymer is prepared in colloidal suspension by chemical oxidation, optionally in the presence of one or more templating agents to maximize the ratio of surface to volume and control the microstructure in the final deposit through control of size and shape of the colloidal particles. For example, in one embodiment the electrochemically-active conducting polymer comprises one or more nanotubes, nano wires, or similar nano-scale structures. The polymer is separated by centrifugation, and washed then resuspended in buffer and the nucleic acid primer is attached. The polymer with attached primer is then deposited onto the carbon working electrode by micropipette or by electrochemical printing.

Other methods for preparing substrates comprising electrochemically-active conducting polymers are well known in the art, and are amenable to use in the preparation of the electrodes of the present invention.

The present invention recognizes that during real time PCR, the composition of the solution steps in a defined way from one cycle to the next. Therefore, signal correlated with a step is derived specifically from the effect of the presence of the nucleic acid target. Since the concentration of target in the solution approximately doubles in each step, the steps are clear and distinct and progress in a well-defined way, and are clearly separable from any general, non-specific drift in the electrochemical properties of the electrode interface. A further advantage is that the high-temperature stage, at 95° C., dissociates nucleic acid from the electrode surface and thus 'resets' the surface. Thus, immediately after this step, the surface is in a defined initial condition of un-hybridised primer/probe. Evolution of the signal from this state, and a systematic change from one cycle to the next, provides another specific indicator of the presence of the target nucleic acid. Thus, the present invention allows specific detection and quantification of target nucleic acid in a small number of cycles—that is, in a time that is significantly shorter than that required for detection and quantification using other methods, such as optical fluorescence methods.

It will be appreciate to those skilled in the art on reading this specification that the electrochemical and mechanical stability of the electrochemical measurement interface upon cycling to the high temperatures necessary to implement PCR is important. In particular, for methods utilizing conducting polymers, irregular or otherwise large changes in adhesion of the polymer to the electrode substrate, or in polymer microstructure, or in state of oxidation or doping of the polymer, is undesirable as it may cause changes in electrochemical reaction rate at the polymer-solution interface that militates against reliable and quantitative measurement.

Exemplary methods and apparatuses of the invention, and applications of such methods and apparatuses will now be described with reference to the following examples.

EXAMPLES

Example One

This example demonstrates the detection of a PCR amplicon using a method of the invention.

Methods

Preparation of Working Electrode

A glassy carbon (GC) working electrode (eDAQ Pty Ltd, 1.0 mm diameter) was cleaned using alumina and washed with Milli-Q water, acetone, ethyl alcohol respectively, then ultra-sonicated in 70% ethyl alcohol for 20 minutes and for 10 minutes in Milli-Q water to remove alumina residues and biological impurities. To analyse the preparation, a cyclic voltammogram (CV) was carried out between −1.0 and 1.0 V in aqueous solution of 5 mM $Fe(CN)_6^{-3/-4}$ for 5 cycles. The electrode was washed with an excess of nuclease-free Milli-Q water. A platinum wire electrode was cleaned with a heat gun and treated with 70% ethyl alcohol then washed with nuclease free Milli-Q water.

The electrochemically-active conducting polymer (ECP) sensor surface was fabricated by electrochemical polymerization onto the glassy carbon electrode. Monomer solution containing 50 mM pyrrole (Py), 1 mM 3-pyrrolylacrylic acid (PAA), 0.1 M KCl in 4 mL phosphate-buffered saline-PBS (pH7.4) and 1 mL acetonitrile (ACN) was bubbled with $N_2$ for 10 minutes. Electrochemical polymerisation was conducted using a three electrode electrochemical cell comprising the GC working electrode (WE), an Ag/AgCl reference electrode (RE) (3 M NaCl, +0.197 V vs; SHE), and a platinum wire counter electrode (CE). A polymerization potential of 1 V (Ag/AgCl) was applied, the cumulative charge passed was measured and the polymerization was terminated at a total charge of 2.0 (±0.5)×$10^{-5}$ C (2.6±0.6 C $cm^{-2}$), which corresponds to an estimated polymer thickness of around 6-12 nm, as estimated from the growth of much thicker layers. Electrodes were evaluated by cyclic voltammetry and electrochemical impedance spectroscopy (EIS).

Electrochemical Measurement

A 2-terminal electrochemical cell was assembled in a 100 µL Eppendorf tube, suitable for insertion into a PCR temperature cycler. The working electrode was the polymer-functionalised GC electrode and the counter/reference electrode was a platinum (Pt) wire. The Pt electrode adopted the redox potential for the ferri-ferrocyanide redox couple (to a reasonable approximation dependent on the current flowing). The instrumentation was a BioLogic Science Instruments type SP-300 potentiostat.

Forward Primer Attachment

For covalent attachment of the forward primer to the electrode surface, the working electrode was immersed in a PBS solution adjusted to pH 5.5 using HCl and containing 80 µM amino-terminated, thymidine 10mer-extended forward primer, 50 mM N-hydroxysuccinimide (NHS) and 50 mM N-(3-Dimethylaminopropyl)-N'-ethylcarbodiimidehydrochloride (EDC), incubated at 28° C. for 2 hours, and then washed with PBS. Successful primer attachment was verified by an observed increase in electrochemical impedance. The impedance diagram could be fitted reasonably with a simple Randles equivalent circuit with the interfacial capacitance modelled as a constant phase element. This indicates that the presence of covalently attached primer increases the charge transfer resistance for the redox couple.

PCR

The PCR reaction mixture comprised PCR buffer (Invitrogen-Life Technologies), $MgCl_2$, platinum Taq polymerase, reverse primer 5'-ATTCCTATGTAGCCGAATG-GTTCTTT-3' [SEQ ID NO. 1] and forward primer, 5'-CGCYTWAACAYTCYGCCATCTTACC-3' [SEQ ID NO. 2], designed for amplification of an 844 base pair region of the mitochondrial cytochrome c oxidase (COI or cox1) gene. The thymidine-extended, amino-terminated forward primer $NH_2$-T10-CGCYTWAACAYTCYGCCATCTTACC [SEQ ID NO. 2] was attached to the electrode surface. Non-complementary bases were chosen as forward and reverse primers to avoid cross contamination and self-hybridization.

PCR Protocol

A PCR master mix was prepared, containing either the reverse primer alone (2-primer system) or both forward and reverse primers (3 primer system) as shown in Table 1. For dilution experiments, the sample DNA solution was diluted as appropriate before addition to the mix.

TABLE 1

| PCR master solutions | | | |
|---|---|---|---|
| | 1-primer | 2-primer | 3-primer |
| PCR buffer: 200 mM Tris-HCl (pH 8.4), 500 mM KCl | 16 µl | 16 µl | 16 µl |
| 50 mM $MgCl_2$ | 8 µl | 8 µl | 8 µl |
| 10 µM forward primer | — | — | 8 µl |
| 10 µM Reverse primer | — | 8 µl | 8 µl |
| 20 mM mixed A, T, C, G nucleotide solution | 1.6 µl | 1.6 µl | 1.6 µl |
| 1 unit/µl Taq polymerase | 1.1 µl | 1.1 µl | 1.1 µl |
| $H_2O$ | 110.9 µl | 110.9 µl | 110.9 µl |
| Sample DNA solution | 6.4 µl | 6.4 µl | 6.4 µl |

Solid potassium ferro- and ferricyanide were added to prepare a solution comprising 5 mM of each. This and, when present, the extracted DNA sample (1.2 ng/μL of chicken blood cell DNA for 1× dilution to 1.2 μg/μL for 1000× dilution) and, when present in the different experiments, reverse primer only or both reverse and forward primers were added at 0.5 μM, and 40 (±0.5) μl of the solution was added to a 100 μL Eppendorf tube comprising the PCR master solution. The tube was then inserted into a PCR temperature cycler. Experiments in the absence of Taq polymerase controlled for non-specific impedance effects during cycling.

The ECP-modified electrode first had impedance measured at 72° C. in the absence of the polymerase enzyme and solution nucleotides, then the ECP-modified electrode and Pt wire were inserted into the tube containing the solution of target DNA, nucleotides, primers and enzyme and 10 μl of mineral oil was overlaid to control evaporation. The tube was sealed with Parafilm®.

The temperature-time profile inside the tube was measured, as follows: initial stabilization at 95° C. took 80 s; temperature stabilization during cycling took 30-35 s. Amplification started with the initialization step at 95° C. for 5 minutes, and then thermo-cycling followed (each time in addition to the measurement and temperature stabilisation time) comprising: denaturation at 95° C. for 30 seconds, annealing at 55° C. for 30 seconds, and extension at 72° C. for 30 seconds. The electrodes were at open-circuit until the measurement was made. Electrochemical impedance measurement at an applied cell potential of +0.23V (ECP vs Pt redox electrode) over the frequency range 100 kHz-1 Hz was made each cycle. Measurement at both 72° C. and 55° C. with different delay times was explored. However, unless otherwise stated, impedance was measured at 72° C. following the 30 s extension time, and took 60 s to complete, and the total time was thus 210 s.

Results
Electrode Selection

The electrode preparation procedure described above resulted in products with some variability. Electrode selection proceeded as follows. Cyclic voltammetry was measured in a PCR cell comprising 40 μl 2.5 mM MgCl$_2$ and 5 mM each of Fe(CN)$_6^{-3/-4}$ in PCR buffer at 72° C. Results are shown in FIG. 1. The effect of the presence of the ECP on the glassy carbon is to increase the reaction impedance for the ferro-ferricyanide couple, as indicated by the increased separation and broadening of the peaks in the voltammogram.

The electrochemical impedance of the ECP-modified electrode compared with bare glassy carbon was measured at a cell potential difference of +0.23 V over a frequency range 100 kHz-1 Hz. The measured impedance was related to the microstructure of the electrode revealed by scanning electron microscopy of the ECP-modified electrode surface as shown in FIG. 2.

The electrochemical impedance was characteristic of a microscopically rough interface, namely a semicircle with centre depressed an angle $n\pi/2$ below the real impedance axis. The maximum value of the imaginary component of impedance, $(-Z''_{max})$ for the approximate equivalent circuit over the frequency range where the diffusional impedance does not affect the data, is $$(-Z'')_{max} = \frac{R_{CT}}{2}\{1 - \sin(n\pi/2)\}. \quad (1)$$

Hence, provided n, which is dependent on the roughness of the interface, does not greatly vary, $(-Z'')_{max}$, (referred to herein as the reaction impedance), is an easily obtained measure of the variation of the resistance due to the charge-transfer reaction of the redox couple, $R_{CT}$. The reaction conductance is herein defined as $\sigma=1/(-Z'')_{max}$. This measure has been used because it is pragmatic and practical, directly reflecting the raw experimental data and not dependent on arbitrary details of a specified equivalent circuit.

The ECP-modified electrodes had a discernable microstructure such that the ECP layer was significantly thicker than the nominal 6 nm calculated from the charge consumed in the preparation of the ECP layer and thus significantly porous. Nodules of polymer were observed scattered across the surface. For some preparations, isolated nodules were much larger than the average, and electrodes having this surface morphology also exhibited two loops in the Nyquist diagram with impedance significantly larger than that shown by the smoother preparations. Electrodes that exhibited large impedance or two distinct loops in the Nyquist diagram were rejected.

Quantification of the Target Concentration

Figure 3:
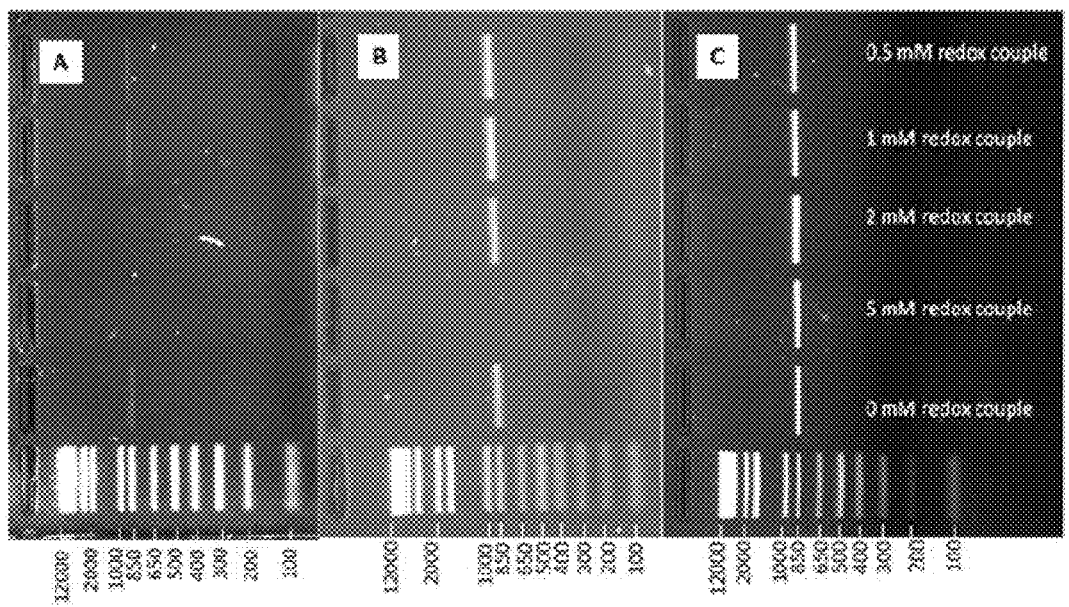
FIGS. 3A-C show gel electrophoresis of PCR solution amplification product (both forward and reverse primer present in solution) showing the effect of redox couple and Taq polymerase concentration. The first lane (lowest) is the scale in base pairs. Taq polymerisation concentration unit/μL, cycle.

Following solution amplification of the Cox1 template present in the chicken blood extract with the same forward and reverse primers used for the electrochemical PCR, the amplified product was separated by gel electrophoresis, extracted, purified and sequenced. The gel electrophoresis (FIG. 3) confirmed clean amplification and the sequencing confirmed amplification of the desired target. When only the reverse primer was present in solution, the generation of the expected solution amplicon (single stranded copies of variable length) only was observed, as confirmed by gel electrophoresis (FIG. 3).

The mass of Cox1 template in the total chicken blood DNA extract was determined using an Applied Biosystems 7900HT Fast PCR System. Quantitative PCR requires a shorter target length than the full 844 bp sequence. To determine a calibration for the system, the amplified and purified oligonucleotide was prepared at known concentration, serially diluted from $4\times10^{-4}$ to $6.4\times10^{-7}$ ng/μL, and used in a qPCR mix containing forward and reverse primers designed to amplify a 119 bp nested product. Chicken blood DNA (30 ng/uL) was run in quadruplicate on the same plate with the same nested primers. Comparison with the standard curve developed from the serial dilutions showed 33 fg/μL of the Cox1 template, or 1 part in $10^6$ of the total chicken blood DNA present. Thus the 1× dilution of total DNA (1.2 ng/μL) contained 1.3 fg/μL or 1450 copies/μL of the Cox1 template.

These results demonstrate that amplification of the target DNA sequence occurs reliably and is not affected by the presence of the redox couple, and establish the high sensitivity of the ePCR method.

Temperature Stability of Electrochemical Behaviour of ECP Electrodes

It was established by cyclic voltammetry that the ECP was indeed reasonably stable at temperatures up to 95° C. provided that the potential range was restricted to less than ±0.4 V with respect to the Fe(CN)$_6^{-3/-4}$ redox electrode to avoid irreversible oxidation or reduction of the polymer. The thermal stability of the ECP electrodes under the proposed conditions of the PCR measurement regime were explored first by EIS measurement in the PCR/redox couple mixture in the absence of target DNA. This measurement also explores the stability of attachment of the primer to the electrode surface. FIG. 4A depicts the variation of the Nyquist diagram of the ECP-modified electrode with attached primer, and shows that electrode impedance changed by less than 20% after 20 temperature cycles. Additionally, cyclic voltammetry of the electrode without attached primer in the absence of the redox couple, measured at 72° C. during the temperature cycling with the electrode otherwise at open circuit, showed very little change in either the apparent capacitance of the electrode or of the redox process of ion injection and removal over 15 temperature cycles as shown in FIG. 4B. The ECP electrode thus appears to be surprisingly more than adequately stable to temperature cycling.

Single-Primer PCR: Amplification from the Surface-Attached Forward Primer Alone

Figure 5B:
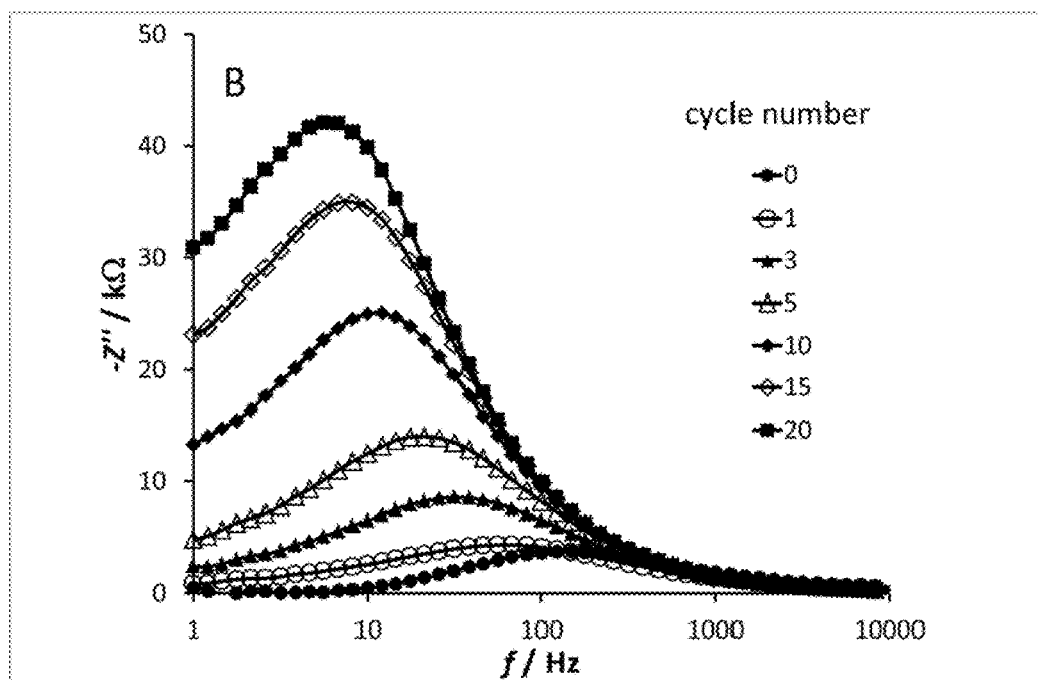
Figure 5C:
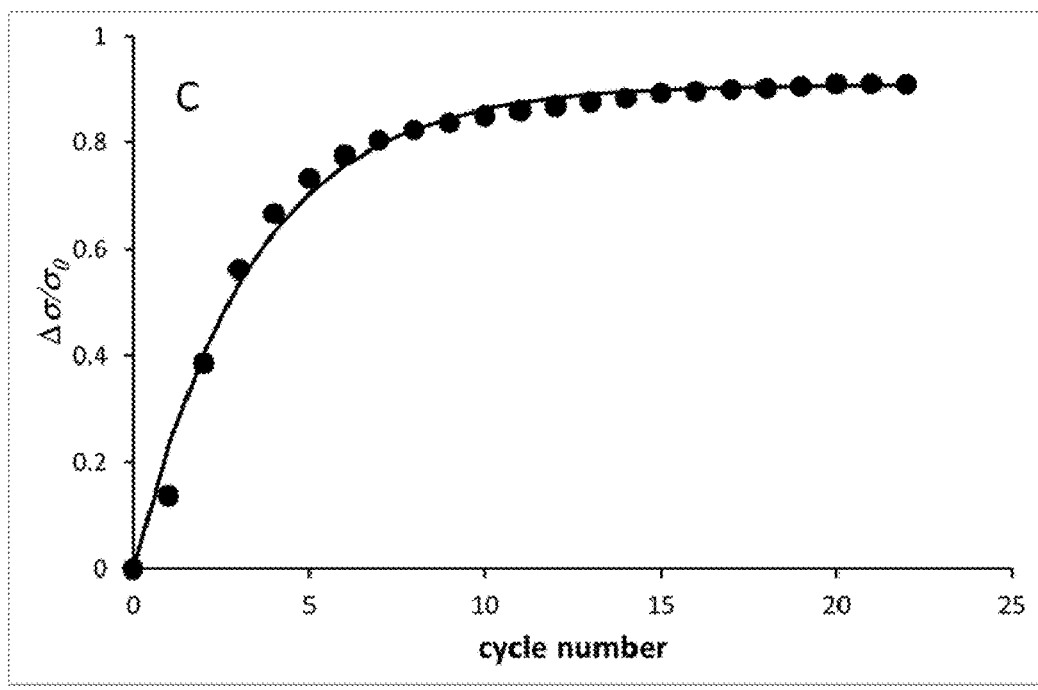

Braslaysky et al have reported that DNA polymerase is active on surface-bound primers. In the absence of the reverse primer in the solution but in the presence of complementary nucleic acid that can hybridise onto the surface-bound primer, the surface-bound primer would be extended to a length determined by the extension time. A statistical distribution of length of surface-bound single-stranded DNA is expected to result. FIG. 5 illustrates that, with the surface-bound primer alone, the impedance signal increased progressively with each temperature cycle. FIG. 5A shows the evolution of the Nyquist diagram with cycle number (cycle 0 is the impedance with the primer attached to the surface, measured in the absence of polymerase enzyme). These diagrams have the form of a distorted semicircle with centre depressed below the real impedance axis. FIG. 5B shows the evolution of the imaginary component of the electrode impedance. The maximum, $-Z''_{max}$, was extracted as convenient empirical estimate of the reaction impedance. FIG. 5C shows the evolution of the reaction impedance expressed as a relative reaction conductance change:

$$\Delta\sigma/\sigma_0 = ((-Z''_{max,cycle\ n}) - (-Z''_{cycle\ 0}))/(-Z''_{max,cycle\ n}) \quad (2).$$

The result is consistent with the reaction impedance for the ferro-ferricyanide redox couple increasing with increasing length of DNA coupled to the surface, and supports a deduction that the mechanism is Donnan exclusion of the redox couple due to increase of surface charge on the electrode.

Figure 7:
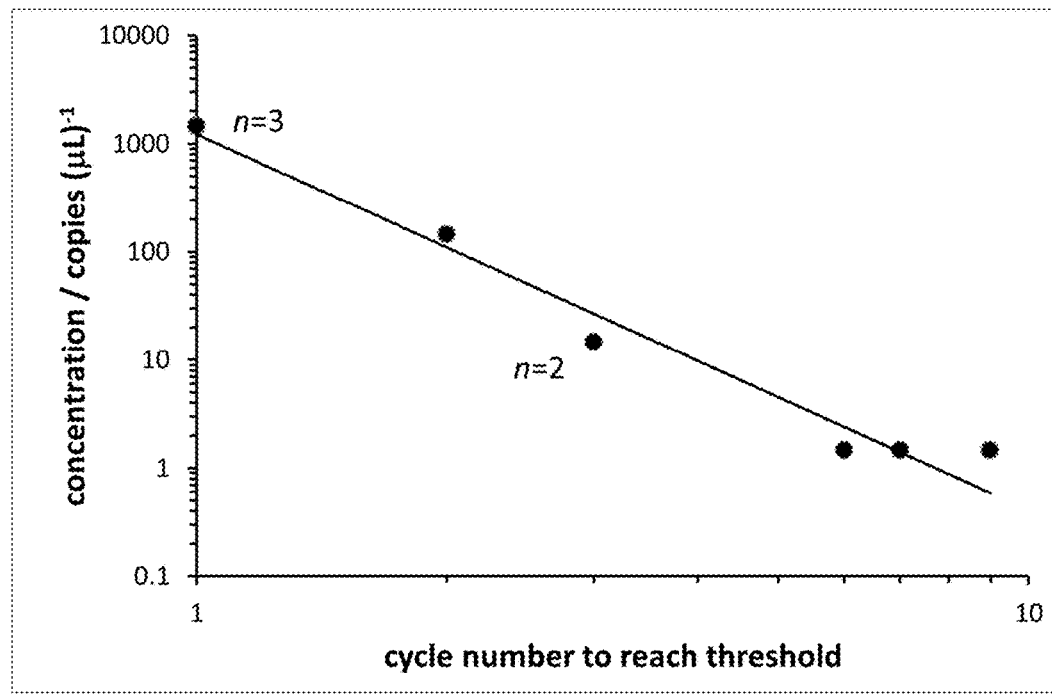
FIG. 7 shows the cycle number to reach Δσ/σ$_0$>0.7, as a function of the concentration of target in the diluted mixed DNA. 3-primer system: both primers in solution and forward primer on electrode. Repeat measurements on independent electrodes at different dilutions from 1× to 1000× of 1.2 ng/mL total DNA (target DNA present at 1 part in 10$^6$ total DNA) are shown; where these overlap, the number of independent determinations is shown.

Electrochemical Measurement of PCR Amplification with Both Primers in Solution, Together with Surface-Bound Forward Primer In this configuration (3 primer system), the target 844 bp sequence is amplified in solution as a double-stranded DNA. In addition, the surface-bound primer may be extended to the 844 bp length defined by the reverse primer present in the solution. Following the dissociation step at 95° C., during the annealing step at 55° C. single stranded DNA from the solution can be hybridized onto the surface-bound oligonucleotide, to both the surface-extended sequence and to any non-extended primer. Impedance diagrams had the same form as FIG. 6. In FIG. 7, the evolution with cycle number of $(-Z''_{max})$ and of the relative reaction conductance is shown.

FIG. 6 illustrates a good reproducibility between different electrode preparations, and very high sensitivity for the method. FIG. 6A shows a comparison of the signal (relative reaction conductance) evolution at 1000× dilution (1.2 pg/μL total DNA; 1.3 ag or 1.5 copies/μL of the mitochondrial DNA target based on the quantification described above) in the presence and absence of the Taq polymerase. The signal for the Taq polymerase-free negative control reached a plateau within the first three cycles. The signal observed in reactions with 1000× dilution of target and Taq polymerase present reproducibly exceeded the negative control within less than 10 cycles, and increased to the same level as that found for the higher concentrations of DNA target. FIG. 6B shows the variation of the raw data—the reaction impedance—at 1000× dilution over the first few cycles, including the Taq polymerase-free blank. It illustrates the significant variation in reaction impedance for the primer-modified electrode (cycle 0) the rapid approach to a plateau in the absence of Taq polymerase and the regular linear increase with cycle number in the presence of Taq polymerase.

These data establish that detection of the presence of the target can be achieved simply by observing the regular increase of reaction impedance with cycle number for a sufficient number of cycles to discriminate against any blank effects.

Quantification can be achieved by counting cycles to reach a threshold relative reaction conductance, as shown in FIG. 7. Such quantification requires the determination of the impedance of the primer-modified electrode before any amplification: $-Z''_{max,cycle\ 0}$ in eq 2. This data further establishes that the method has extremely high sensitivity obtainable in a small number of PCR cycles. The timescale for quantification at the highest dilution, with target concentration in the 2 copies/μL or fg/mL range was 25 min (7 cycles). Given a significant part of these times was that for temperature stabilization, which can be mitigated by appropriate design of the cell and cycler, and for measurement of the full impedance spectrum, which is unnecessary in many implementations, a significant reduction in processing and thus detection time is achievable.

Electrochemical Measurement of PCR Amplification with Just Reverse Primer in Solution, Together with Surface-Bound Forward Primer In this configuration, the surface-bound primer may be extended to the 844 bp length defined by the reverse primer present in the solution, as above. However, in the solution, single-stranded DNA will be formed by reaction from the single primer present, to a length defined by the extension time. This single-stranded DNA can be captured onto the surface-bound oligonucleotide during the annealing step at 55° C. Impedance diagrams had the same form as illustrated in FIG. 5, and reaction impedance evolved with cycle number in a similar way to that shown in FIGS. 5 and 6.

Effects of Changing Measurement Temperature and Time Delay Before Measurement

Figure 8:
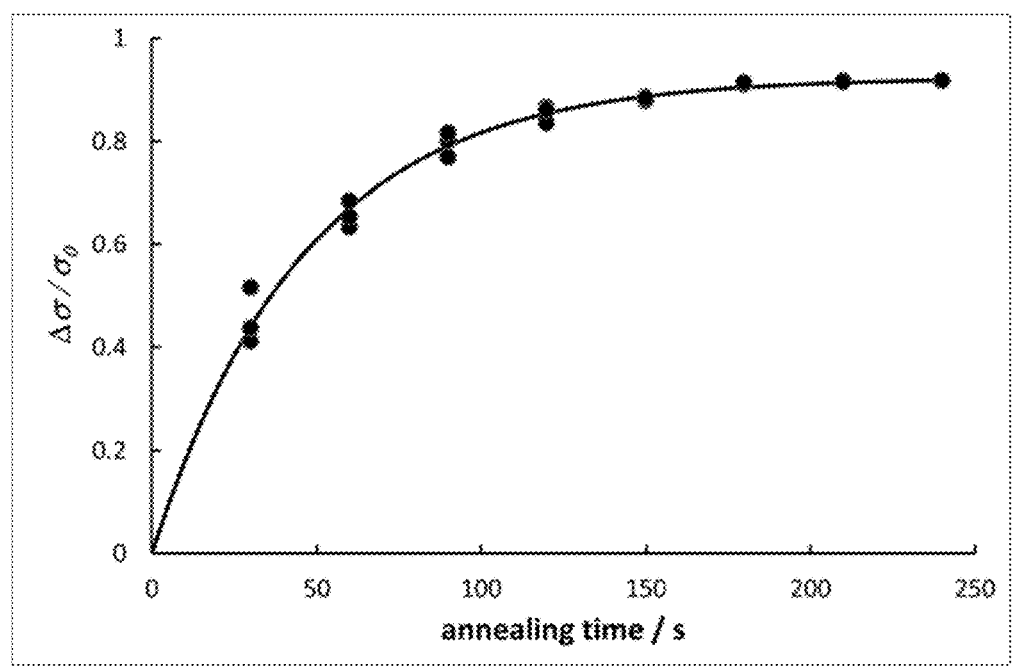
FIG. 8 is a graph showing the change in relative reaction conductance (eq 2) at 55° C. with annealing time at this temperature following a step from 95° C. Impedance measured in the PCR buffer containing 5 mM redox couple in the 2-terminal cell with cell potential difference +0.23 V, in the absence of Taq polymerase. Total chicken blood DNA concentration 1.2 ng/μL (target DNA present at 1 part in $10^6$ total DNA). The line is the fit to a simple exponential approach to a limit (see Discussion). Reaction conductance, $\sigma_0$, of the forward primer-modified electrode measured in the absence of DNA: 1600Ω; projected from fit: 1100Ω.

It is to be expected that the measurement signal would be altered as a consequence of the effects of the kinetics of the polymerase reaction both in the solution and on the electrode surface, and of the effects of diffusion of single-stranded DNA to the electrode surface, of the kinetics of hybridization to the surface-bound oligonucleotide, and of the competition for dissociated single-stranded DNA between solution hybridization and surface hybridisation. The measurement could also just as conveniently by made at the end of the annealing step at 55° C. as at the end of the extension step at 72° C. FIG. 8 shows the effect of changing the annealing time, with measurements made for three successive temperature cycles between 95° C. and 55° C. In this experiment, Taq polymerase was absent; the forward primer was present on the electrode surface. In the presence of the mixed DNA, the temperature was stepped to 95° C. to dissociate surface-hybridised DNA. Then the temperature was stepped back to 55° C. and successive impedance measurements made at that temperature as the annealing proceeded. FIG. 8 shows that the change in relative reaction conductance approached a limit with a time constant of approximately 84 s. Similarly, increase of the extension time at 72° C. gave an increase of reaction impedance. The choice of extension and annealing time represents a compromise between signal development at each cycle, stability of the electrochemical impedance during the time that the measurement is made, and the number of cycles that can be completed within a given analysis time.

The reaction conductance, $\sigma_0$, of the forward primer-modified electrode measured in the absence of DNA can be obtained by fitting the annealing time dependence of the relative reaction conductance to a simple exponential evolution with time, albeit not with great accuracy given the time resolution of the measurements performed herein.

The voltammetry showed an increase in charge transfer resistance for the ferro-ferricyanide redox couple when the conducting polymer film was present. Although the polymer film was nominally only 6-12 nm thick, if the growth charge were to form a dense layer, the microscopy indicates a thickness that is much greater. The impedance diagrams are also characteristic of a porous structure. The impedance diagrams reflected the microstructure of the polymer interface, which was microscopically inhomogeneous.

Discussion

The data presented herein clearly establishes that a label-free electrochemical method utilizing exclusion of a redox couple from the surface of an electrochemically active conducting polymer can be used as a high-sensitivity real-time measurement of the progress of PCR amplification of a minor component from mixed DNA. FIG. 7 illustrates that quantitation can be achieved by counting cycles to reach a threshold, and that the method has extremely high sensitivity obtainable in a small number of PCR cycles. The timescale for quantification at the highest dilution, with target concentration in the 2 copies/µL or fg/mL range was 25 min (7 cycles).

FIG. 6 illustrates that the blank signal, in the absence of Taq polymerase, increased over the first 2 or 3 cycles and then stabilised. Although there may be some non-specific binding of non-target DNA, this effect is minimised through the design of PCR templates and the use of elevated temperatures. In such circumstances, the signal in the absence of Taq polymerase is interpreted as being due to binding of the target, the extent of which depends on the concentration of target in the boundary layer near the electrode and which increases over the first few cycles as a consequence of dissociation from the surface of previously bound DNA, during the 95° C. part of the cycle.

This work has shown an adequate temperature stability of the ECP in aqueous buffer for use in amplification methods of the invention, for example using the system employed here. Without wishing to be bound by any theory, three factors are believed to be important: the conducting polymer layer was very thin; the synthesis used a solvent that was dominantly water with just a small addition of organic solvent; and the ions doped into the polymer during synthesis were the same as those dominantly present in the measurement solution.

In the following, the above results are discussed using the simple patch model for the electrochemical kinetics wherein the total current through the interface is the sum of that through different patches carrying different surface charge.

FIG. 8 illustrates the simplest case: the annealing of the target sequence onto the surface primer, which is the first step of the first cycle. In this case, the surface-bound primer captures onto the interface the entire single DNA strand within which the complementary sequence is embedded. A two-patch model applies, with one patch being the hybridized fraction of the surface and the other being the unhybridized fraction. The conductance, $\sigma$, due to the interface reaction is the sum of the conductance through the unhybridized patches, $\sigma_0$, and that through the hybridized patches, $\sigma_1$:

$$\sigma = \theta_0 \sigma_0 + (1-\theta_0)\sigma_1 \quad (3),$$

where $\theta_0$ denotes the fraction of the surface that is not hybridized. The variation with time, t, of the relative change in reaction conductance during the annealing step, where the reaction conductance for the state with unhybridized surface-attached primer only is $\sigma_0$, shows the progressive coverage of the surface by hybridized DNA. FIG. 8 indicates that this is a simple first order kinetic process with time constant $\tau$:

$$\Delta\sigma/\sigma_0 = (1-\theta_0)(1-(\sigma_1/\sigma_0)) = (1-\sigma_1/\sigma_0)\{1-\exp(-t/\tau)\} \quad (4).$$

The significance is that extrapolation back to the reaction impedance at t=0 during annealing at 55° C. following the initialization of the sequence at 95° C. gives $\sigma_0$, the reaction conductance for the state with unhybridized surface-attached primer only, obviating the need for prior measurement of this number, which is variable from one electrode to another (FIG. 6B) but is also key to reducing the data onto the repeatable curve of relative reaction conductance against cycle number (FIG. 6A).

The simplest measurement system of those studied here is that where the only primer is that bound to the surface: the results are shown in FIG. 5. The increase in reaction impedance (decrease in reaction conductance) on each cycle, shown in FIG. 5, is interpreted as being due to the progressive extension of surface-bound primer. After dissociation then annealing, complementary single-strand DNA from the solution is annealed to the surface-bound primer. In the extension step, the hybridized, surface-bound primer is extended to an extent dependent upon the extension time and the length of the hybridized complementary sequence, which is limited only by the length of the original DNA since there is no second primer present in the solution. The cycle then repeats, upon which complementary oligonucleotide can be captured both onto the extended and un-extended surface-bound primers. The theoretical curve for the evolution of relative reaction conductance with cycle number, shown in FIG. 5C, was derived by approximating the heterogeneous collection of extended primer and extended, hybridized primer states as a single low-conductance state. The model is thus a simple 2-state model. The progression from state 0, unreacted primer, to state 1, reacted primer, is presumed to occur by a simple first-order process during both annealing and extension. To simplify further, just one of these steps is assumed to be rate limiting and in view of the result of FIG. 8 it can be assumed that this is the annealing step. Thus, following step n, where t denotes the annealing time for each step $$\theta_{1,n} = \theta_{0,n-1}\exp(-t/\tau) \quad (5).$$

The reaction conductance at each step is the sum of that due to state 1 and that due to state 0 (eq 3). The data can then be fitted with the two parameters $t/\tau$ and $\sigma_1/\sigma_0$, as shown in FIG. 5C. For both the data in FIG. 5 and that in FIG. 8, $\sigma_1/\sigma_0 \approx 0.09$. The redox couple is relatively strongly excluded from the interface as a consequence of the surface charge due to the surface-bound primer and DNA. This effect is believed, again without wishing to be bound by any theory, to explain why the electrochemical surface extension proceeded satisfactorily despite the effect of the redox couple on the solution extension (FIG. 3).

Figure 9:
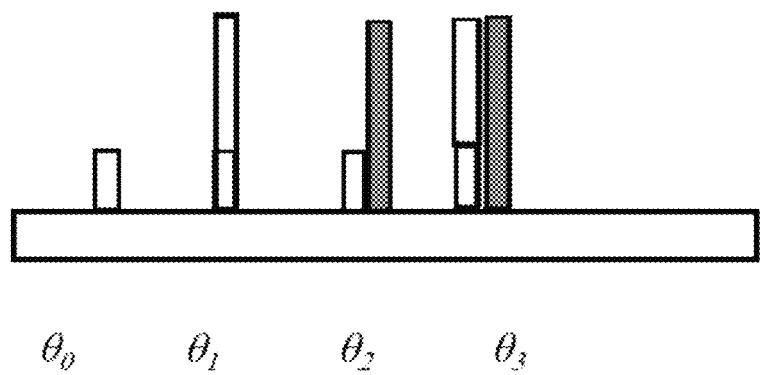
FIG. 9 is a schematic representation of the states for the surface-bound DNA, and the transitions during the PCR cycle; $\theta_j$ denotes the fraction of the surface covered by state j.

In the 3-primer system (results shown in FIGS. 6 and 7) amplification should occur in the solution as well as extension on the surface. In the solution, the system would evolve rapidly to a multiplication of the fixed-length target DNA segment, whose concentration increases in each cycle: $c_{target,n} = \alpha^n c_{target,0}$ where the multiplication factor, $\alpha \approx 2$ is expected for the ideal case. Amplification of the target DNA sequence in the solution should lead to an increase of sensitivity above that obtained when the only effect is extension of the primer on the surface: indeed this effect was observed. In this case, to take into account both the effect of extension of the primer on the surface and the effect of capture onto the surface of amplicons from the solution, the surface can be represented by a 4-state model as indicated in FIG. 9: state 0 is the un-extended, un-hybridized surface-attached primer; state 1 is extended, un-hybridized surface-attached primer; state 2 is un-extended surface-attached primer hybridized to complementary target from the solution; and state 3 is extended, surface-attached primer hybridized to complementary target from the solution. After the denaturation step at 95° C., only states 0 and 1 are present on the surface; states 2 and 3 are formed at 55° C. by annealing from the solution remaining from the previous extension step. In the subsequent extension step at 72° C., conversion of state 2 to state 3 by the Taq polymerase occurs as well as multiplication in the solution.

To take account of the effect of increase of solution amplicon concentration with cycle number, it is assumed that, during the annealing and extension phases, for the states j=0, 1 where target DNA is captured onto the surface from the solution:

$$\left(\frac{d\theta_j}{dt}\right)_{cycle\ n} \approx -\alpha^n c_{target,0}/\tau = -\alpha^n/\tau', \quad (6)$$

with time constant, $\tau'$, independent of cycle number. For each cycle, the system is re-initialised to a condition with no captured DNA—ie just states 0 and 1—at the end of the denaturing phase at 95° C. Hence, using the subscript d to denote the relative surface coverages of states j=0 at the end of the denaturing phase, in view of eq 6 we write $$(\theta_{0,d})_{cycle\ n} = (\theta_{0,d})_{cycle\ n-1} \exp(-\alpha^{n-1}/\tau') \quad (7)$$

$$(\theta_{1,d})_{cycle\ n} = 1 - (\theta_{0,d})_{cycle\ n} \quad (8).$$

Then, using the subscript e to denote the state of the system at the end of the extension phase at 72° C., for states j=0, 1:

$$(\theta_{j,e})_{cycle\ n} = (\theta_{j,d})_{cycle\ n} \exp(-\alpha^n/\tau') \quad (9).$$

The relative coverage of the other states, j=2,3, is then obtained because these are derived by conversion of states 0 and 1 during annealing and extension $$(\theta_{2,e})_{cycle\ n} = (\theta_{0,d})_{cycle\ n} - (\theta_{0,e})_{cycle\ n} \quad (10)$$

$$(\theta_{3,e})_{cycle\ n} = (\theta_{1,d})_{cycle\ n} - (\theta_{1,e})_{cycle\ n} \quad (11)$$

The reaction conductance is expressed as the sum of that from each of the individual states. FIG. 6B shows the result of a least-squares fit to the experimental data of the relative reaction conductance thus predicted. The derived parameters for simple 4-state model for the system with both primers in solution and forward primer surface-attached are given in Table 2.

TABLE 2

4-state model parameters.

| Relative concentration | $\tau'$/cycle | $\alpha$ | state | Relative conductance |
|---|---|---|---|---|
| 1 | 0.75 | 1.08 | 0 | 1 |
| 0.1 | 0.93 | 1.1 | 1 | 0.6 |
| 0.01 | 1.4 | 1.15 | 2 | 0.6 |
| 0.001 | 2.9 | 1.14 | 3 | 0.02 |

Figure 10:
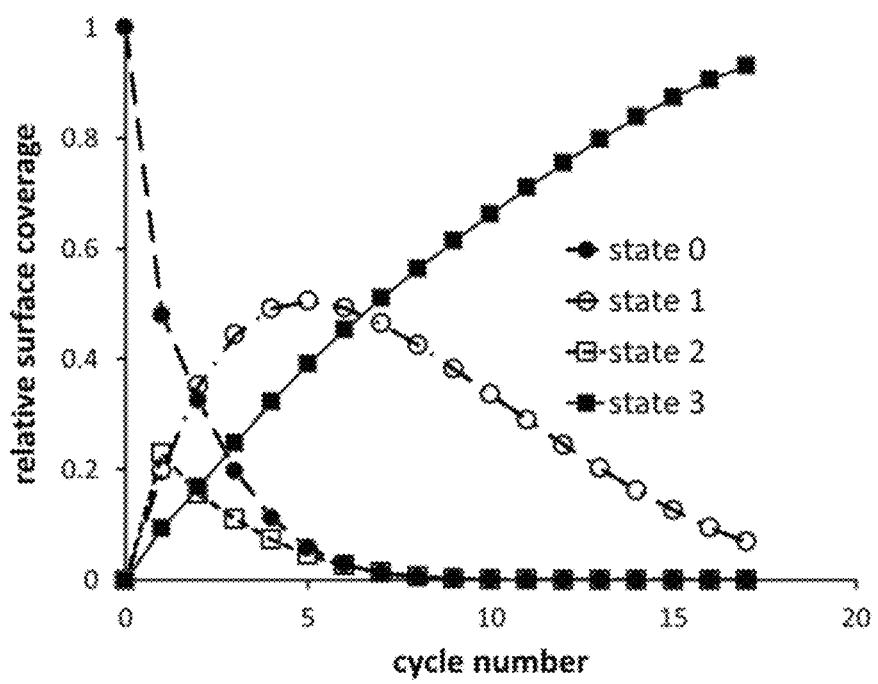
FIG. 10 shows the evolution of relative surface coverages for the simple 4-state model at dilution 1000× of total mixed DNA (relative concentration 0.001: data from FIG. 6).

FIG. 10 shows the derived variation of the relative coverage of the 4 different states as the PCR cycling proceeds, for a sample where the total mixed DNA was diluted 1000×. Although the model is clearly over-simplified (eg $\tau'$ does not increase as expected with decrease of target concentration) the derived parameters allow some discussion of features of the results. First, the multiplication factor, $\alpha$ is significantly less than 2, which is consistent with the effect of the redox couple on the solution amplification. This effect can be mitigated, as implied by FIG. 3, by either increasing the concentration of the Taq polymerase or decreasing the concentration of the redox couple. Such alterations however, involve compromises of cost (of Taq polymerase) and signal/noise (in the impedance measurement). Second, the signal development is dominated in the early cycles by the effect of extension of the surface primer and then in the later stages of the amplification by the capture of amplicons from solution. This is reasonable and accounts for much of the difference between the results of FIG. 5 and FIG. 6. Third, the relative conductances due to states 1 and 2 are much greater than those suggested by the fitting of the two-state model to the data of FIGS. 5 and 8. This reflects both deficiencies of the model and subtleties in the evolution of the system that differs according to whether primers are present in the solution or not. The length to which the enzyme can extend the surface-attached primer is determined by the length of the complementary strand hybridized to it. With no solution primers, this can proceed in principle to as much as the total length of the DNA sequence within which the target is embedded. However, with both primers present in solution, the target sequence itself will become the dominant complementary strand after a few cycles, resulting in the surface primer being extended only to the length of the target.

The discussion highlights that the high-temperature stage, at 95° C., dissociates the untethered complimentary DNA strand from the surface. The surface is thus 'reset'. Thus, immediately after this step, the surface is in a defined reset condition of un-hybridized primer, both extended and un-extended in proportion depending on the number of prior amplification cycles. Evolution of the signal from this 'reset' state, and a systematic change from one cycle to the next, should thus provide another specific indicator of the presence of the target DNA.

Example Two

This example demonstrates the preparation of an electrode for use in embodiments of the invention coated with a pyrrolylbutyric acid conductive polymer.

A 2-terminal electrochemical cell having a carbon working electrode with a rough surface was prepared as follows. A gold electrode was evaporated onto a plastic base. Carbon ink ('wirebond' diluted with ethanol) was painted over the gold and smoothed off. An insulator was deposited to entirely cover the carbon layer and a second gold electrode was evaporated on top. A UV laser was used to punch holes through the top electrode and the insulator layer into the carbon layer beneath: a 2-terminal electrochemical cell was thus prepared. A plastic cylinder was glued on top so as to make a container that held electrolyte in contact with the electrode assembly.

The rough carbon electrode was coated with a thin layer of a copolymer of pyrrole (Py) and 4-(3-Pyrrolyl)butyric acid (PBA) by electrochemical polymerisation. A solution comprising 8 µL PCR buffer (200 mM Tris-HCl, pH 8.4, 500 mM KCl), 4 µL $MgCl_2$ solution (25 mM) and 68 µL of a solution containing 0.1 M NaCl, 1 mM PBA and 50 mM Py in water was added into the cell. A potential difference of 1V was applied between the electrodes for 1 s after which the cell was rinsed out with water and dried with a stream of nitrogen gas. The cell was then filled with the primer oligonucleotide attachment solution: 12.5 µl EDC (400 mM, in phosphate buffer pH 5.2), 12.5 µl NHS (400 mM in phosphate buffer pH 5.2), 1 µl primer oligonucleotide (400 µM), 24 µl phosphate buffer pH 5.2, covered with parafilm then left for 1 hr at room temperature.

The cell was then rinsed with water, clamped to the face of a temperature-controlled heater and the PCR reaction sample solution added: 4 µl PCR buffer, 2 µl $MgCl_2$ (50 mM), 2 µl 10 µM forward primer, 2 µl 10 µM reverse primer, 0.4 µl 20 mM mixed nucleotide solution, 4 µl (4 U/µl) Taq polymerase, 22 µl water, 1.6 µl (3 ng/µl) target DNA sample, 2 µl $Fe(CN)_6^{-3/-4}$ stock solution (100 mM). Paraffin oil was added to cover the surface of the solution. The temperature was cycled (95° C.-55° C.-72° C.) and the impedance of the electrochemical cell was continuously measured over the frequency range 8 kHz-0.5 Hz at a cell potential, difference of +0.23 V.

The impedance steadily increased with each successive temperature cycle.

INDUSTRIAL APPLICABILITY

The methods and apparatuses of the invention are useful for amplifying, detecting, identifying and quantifying nucleic acids, and have application in diverse industries including the medical, agricultural, pharmaceutical, biotechnological, and security fields.

The invention claimed is:
1. A method for amplifying a target nucleic acid, the method comprising the steps of
 a) providing a reaction volume comprising
  (i) a first electrode comprising an electrochemically-active conducting polymer,
  (ii) a first single-stranded nucleic acid molecule capable of hydridizing to a first portion of a target nucleic acid sequence, wherein the first nucleic acid molecule is covalently attached to the electrochemically-active conducting polymer, and
  (iii) a second electrode;
 b) providing a reaction mixture to the reaction volume, the reaction mixture comprising
  (i) the target nucleic acid,
  (ii) a second single-stranded nucleic acid molecule comprising nucleic acid sequence complementary to a second portion of the target nucleic acid sequence,
  (iii) a nucleic acid polymerase,
  (iv) ferro-ferricyanide, and
  (v) a supply of reagents for a nucleic acid amplification reaction;
 c) performing a polymerase chain reaction, and
 d) measuring the impedance of the first electrode at least once during the polymerase chain reaction.

2. The method of claim 1 wherein the reaction mixture comprises the first single-stranded nucleic acid molecule, or a single-stranded nucleic acid molecule capable of hydridizing to the first portion of the target nucleic acid sequence.

3. The method of claim 1 wherein the method comprises the additional step of determining the presence or amount of polynucleotide in the reaction volume on the basis of the one or more impedance measurements.

4. The method of claim 1 wherein the method comprises the additional step of measuring the impedance of the first electrode before the first elongation step of the polymerase chain reaction.

5. The method of claim 1 wherein the impedance is measured continuously throughout at least a portion of the polymerase chain reaction.

SEQUENCE LISTING

<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide primer synthesised
      in laboratory

<400> SEQUENCE: 1
attcctatgt agccgaatgg ttcttt                                        26

<210> SEQ ID NO 2
<211> LENGTH: 25
<212> TYPE: DNA
<213> ORGANISM: Artificial
<220> FEATURE:
<223> OTHER INFORMATION: Synthetic oligonucleotide primer synthesised
      in laboratory

<400> SEQUENCE: 2
cgcytwaaca ytcygccatc ttacc                                         25

6. The method of claim 1 wherein the electrochemically-active conducting polymer is selected from the group consisting of electrochemically-active conducting polymers that are or comprise a poly-pyrrole or a derivative thereof, a pyrrolylacrylic acid, poly-3-pyrrolylacrylic acid, pyrrolyl-butyric acid, poly-4-(3-pyrrolyl)butyric acid, a co-polymer of poly-pyrrole and 3-pyrrolacrylic acid, a co-polymer of poly-pyrrole and 4-(3-pyrrolylbutyric) acid, a poly-thiophene or a derivative thereof, 3,4-ethylenedioxythiophene, poly(3,4-ethylenedioxythiophene), or a poly-aniline or a derivative thereof.

7. The method of claim 6 wherein the electrochemically-active conducting polymer comprises both pyrrole and thiophene.

8. The method of claim 1 wherein the target nucleic acid is present at an initial concentration of less than 1 pg/mL.

9. The method of claim 8 wherein the target nucleic acid is present at an initial concentration of less than 1 fg/mL.

* * * * *